(12) United States Patent
Tajima

(10) Patent No.: US 9,797,008 B2
(45) Date of Patent: Oct. 24, 2017

(54) AUTOMATED NUCLEIC ACID PROCESSOR AND AUTOMATED NUCLEIC ACID PROCESSING METHOD USING MULTI FUNCTION DISPENSING UNIT

(71) Applicant: Universal Bio Research Co., Ltd., Matsudo-shi, Chiba (JP)

(72) Inventor: Hideji Tajima, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 224 days.

(21) Appl. No.: 14/707,900

(22) Filed: May 8, 2015

(65) Prior Publication Data

US 2015/0315630 A1  Nov. 5, 2015

Related U.S. Application Data

(62) Division of application No. 13/879,069, filed as application No. PCT/JP2011/073697 on Oct. 14, 2011, now Pat. No. 9,057,101.

(30) Foreign Application Priority Data

Oct. 15, 2010 (JP) ................. 2010-233057

(51) Int. Cl.
| | |
|---|---|
| *C12Q 1/68* | (2006.01) |
| *G01N 21/75* | (2006.01) |
| *B01L 7/00* | (2006.01) |
| *B01L 3/02* | (2006.01) |
| *G01N 35/00* | (2006.01) |
| *G01N 35/04* | (2006.01) |
| *G01N 35/10* | (2006.01) |
| *B01L 3/00* | (2006.01) |

(52) U.S. Cl.
CPC ............ *C12Q 1/686* (2013.01); *B01L 3/0217* (2013.01); *B01L 3/0275* (2013.01); *B01L 7/52* (2013.01); *C12Q 1/6806* (2013.01); *G01N 21/75* (2013.01); *G01N 35/00732* (2013.01); *G01N 35/04* (2013.01); *G01N 35/1065* (2013.01); *B01L 3/523* (2013.01); *B01L 3/527* (2013.01); *B01L 2200/026* (2013.01); *B01L 2200/0689* (2013.01); *B01L 2200/142* (2013.01); *B01L 2300/024* (2013.01); *B01L 2300/044* (2013.01); *B01L 2300/0654* (2013.01); *B01L 2300/0672* (2013.01); *B01L 2300/0829* (2013.01); *B01L 2300/1822* (2013.01); *B01L 2300/1888* (2013.01); *C12Q 2563/143* (2013.01); *C12Q 2563/149* (2013.01); *C12Q 2565/629* (2013.01); *G01N 2035/00742* (2013.01); *G01N 2035/00821* (2013.01); *G01N 2035/00851* (2013.01); *G01N 2035/0403* (2013.01); *G01N 2035/103* (2013.01); *G01N 2035/1048* (2013.01); *G01N 2035/1055* (2013.01); *G01N 2035/1062* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,846,489 A | 12/1998 | Bienhaus et al. |
| 5,958,349 A | 9/1999 | Petersen et al. |
| 2003/0162285 A1 | 8/2003 | Tajima |

FOREIGN PATENT DOCUMENTS

| | | |
|---|---|---|
| JP | 2005-95134 | 4/2005 |
| WO | WO 97/46712 | 12/1997 |

OTHER PUBLICATIONS

Tajima, Hideji, "System for Automated DNA Extraction Using Magnetic Particles", Journal of Magnetics Society of Japan, 1998, vol. 22, No. 5, pp. 1010-1015.
International Preliminary Report on Patentability Chapter II for PCT/JP2011/073697 by IPEA/JP, and English translation, dated Sep. 4, 2012.
International Search Report for PCT/JP2011/073697 by ISA/JP, and English translation, dated Dec. 20, 2011.
Written Opinion of the International Search Authority for PCT/JP2011/073697 by ISA/JP, dated Dec. 20, 2011.

*Primary Examiner* — David Thomas
(74) *Attorney, Agent, or Firm* — Haynes and Boone, LLP

(57) ABSTRACT

In relation to an automated nucleic acid processor and an automated nucleic acid processing method using a multi function dispensing unit, processing involving extraction and amplification of the nucleic acid, can be consistently, quickly and efficiently conducted at a low cost with the use of a multi function dispensing unit, while saving user's trouble without expanding the scale of the device. The multi function dispensing unit includes: a nozzle head provided with a suction-discharge mechanism and nozzles detachably provided with dispensing tips; a container group having, at the very least housing parts for liquids and reaction containers for housing an amplification solution; a transfer mechanism that makes an interval between the nozzles and the container group relatively movable; a temperature controller whereby temperature control of the interior of the reaction vessels is possible; sealing liquids and/or sealing lids that are transportable to the reaction vessels using the nozzles, and which make the amplification solutions housed in the reaction vessels sealable within the reaction vessels; and a sealing control part that controls the suction-discharge mechanism or the transfer mechanism, such that the sealing liquid and/or the sealing lids seal the amplification solution within the reaction vessels when the housing of the amplification solution in the reaction vessels is completed.

11 Claims, 19 Drawing Sheets

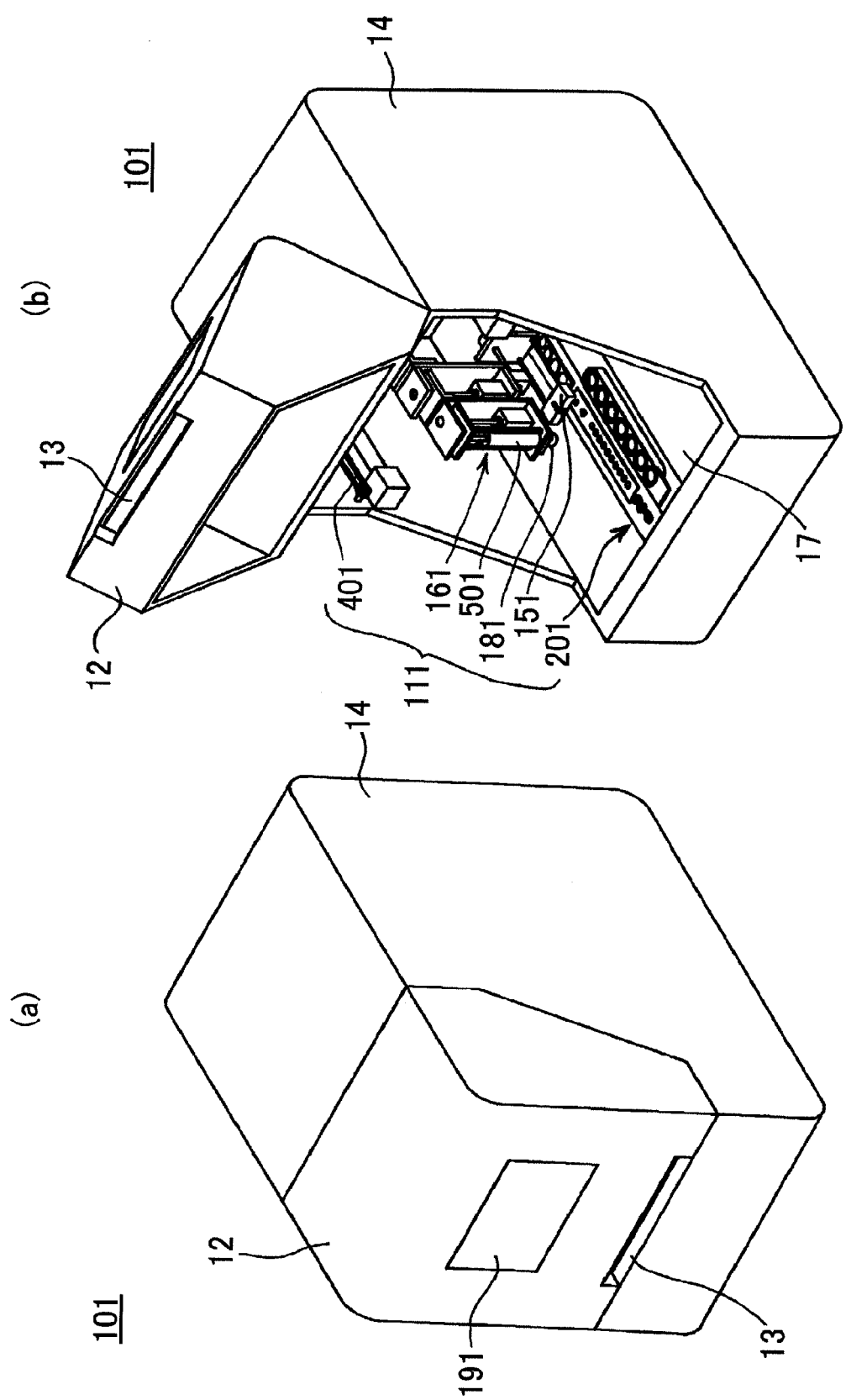
[Fig. 2]

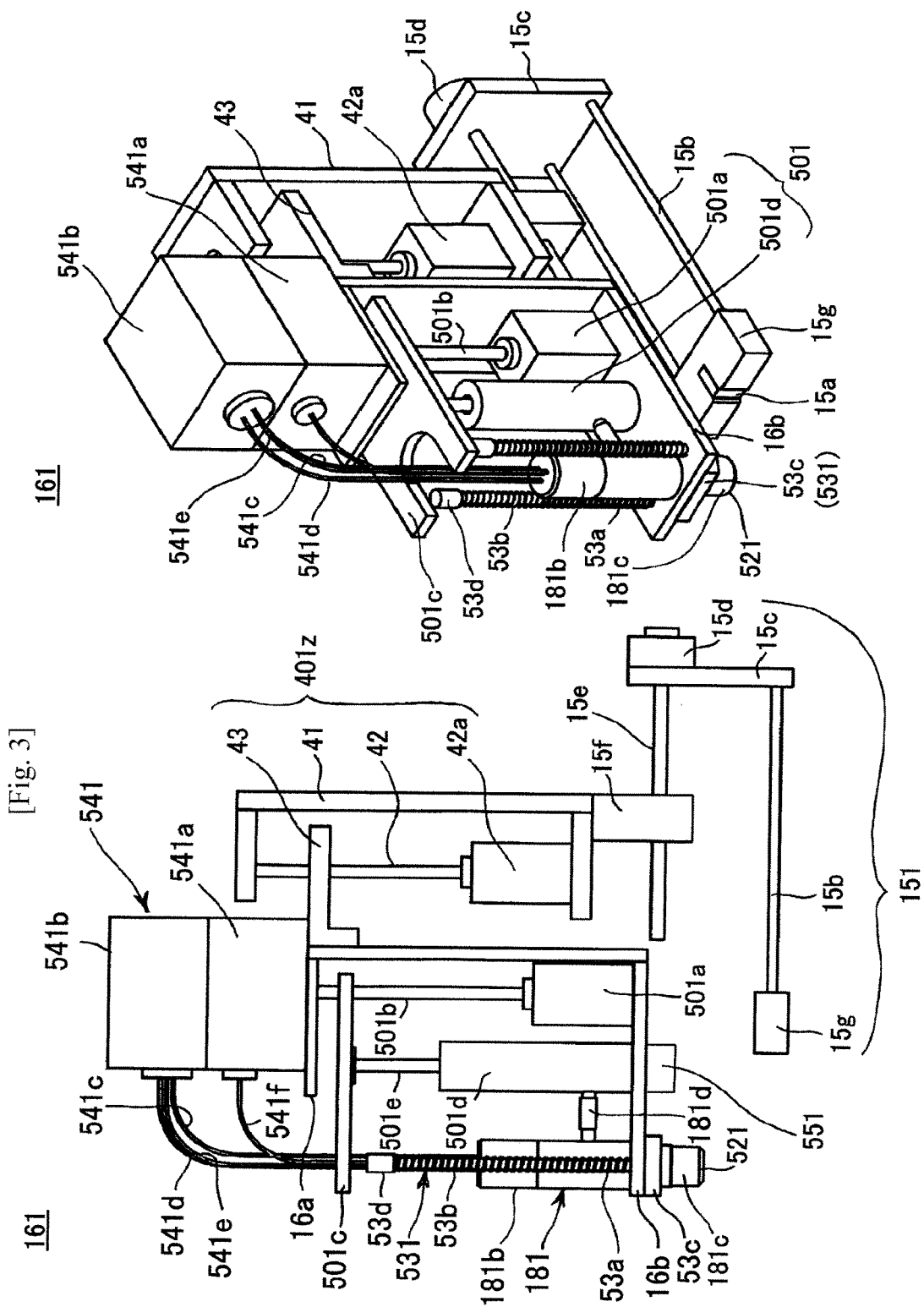

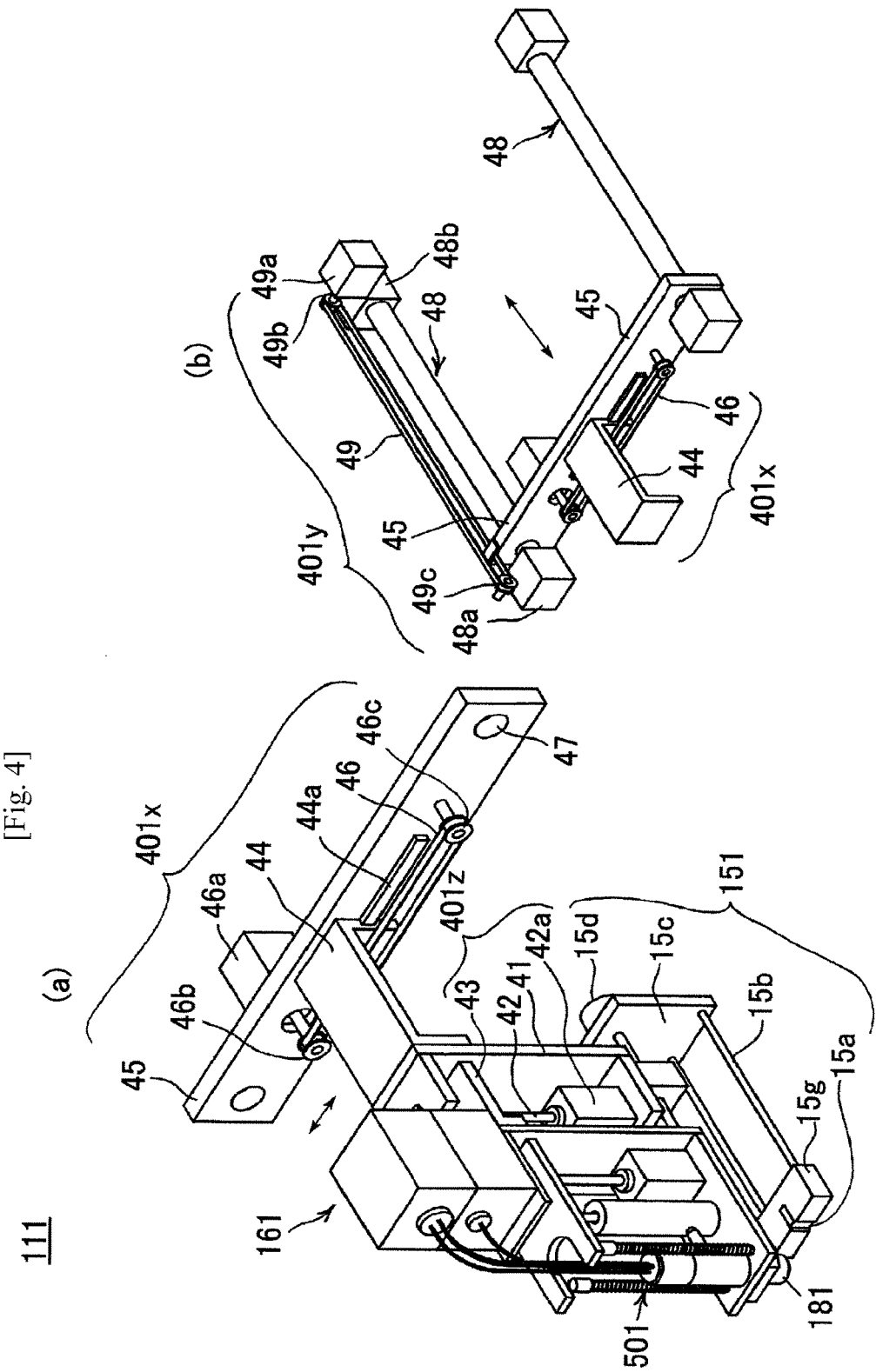
[Fig. 4]

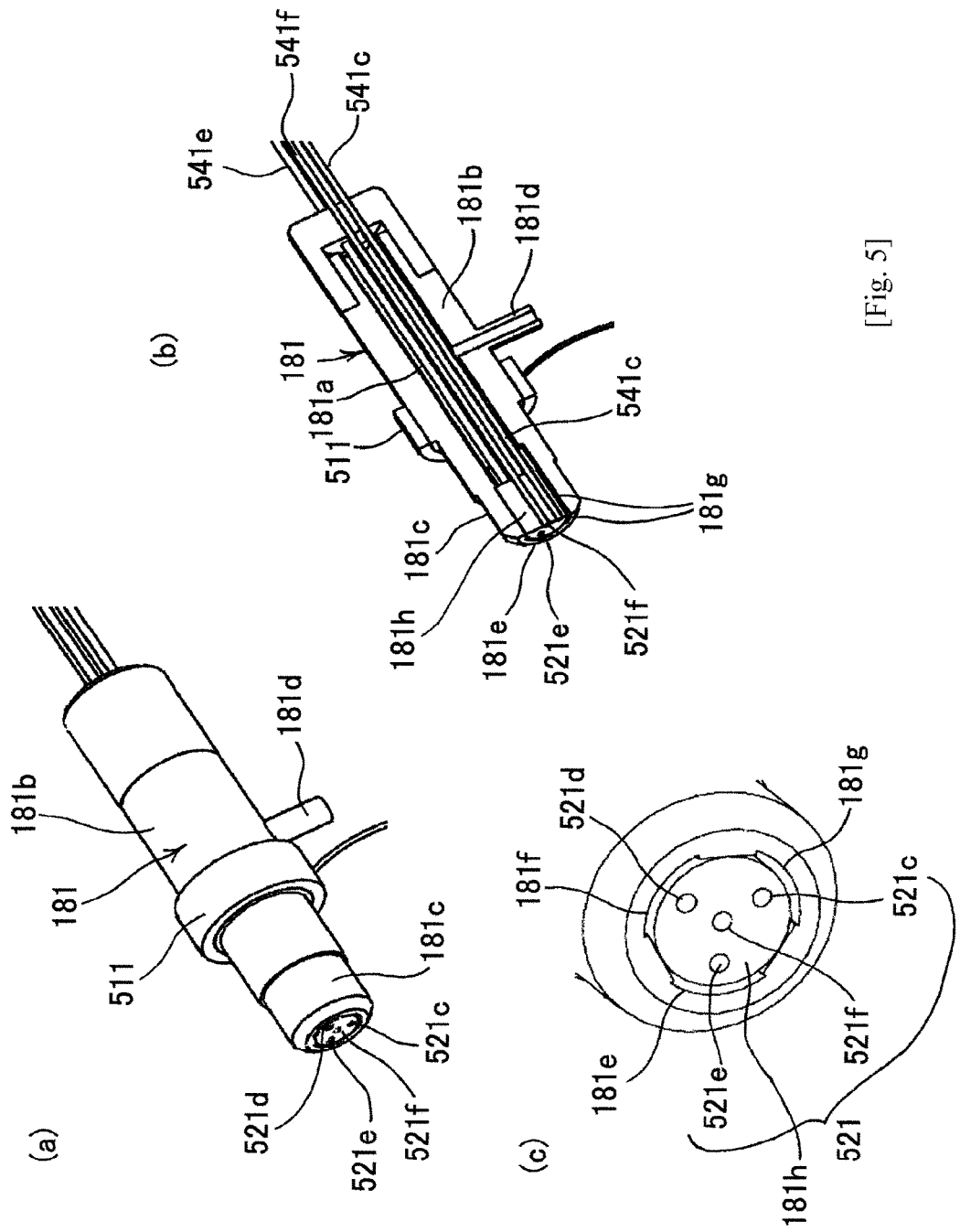
[Fig. 5]

[Fig. 6]
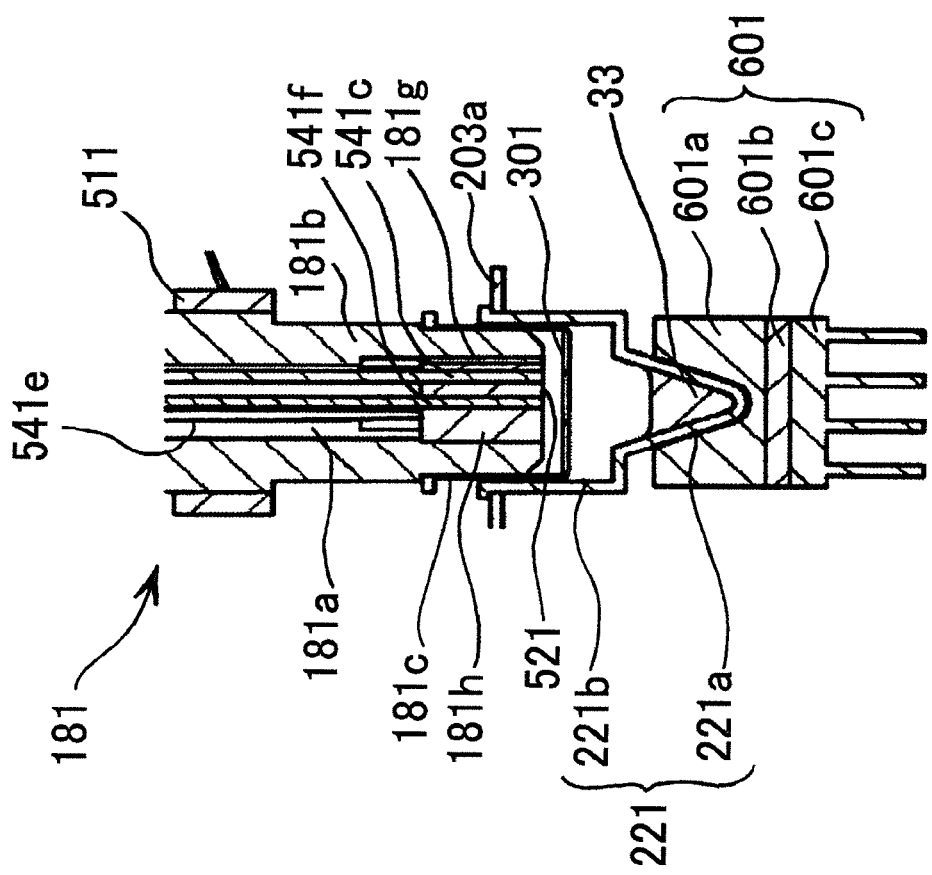

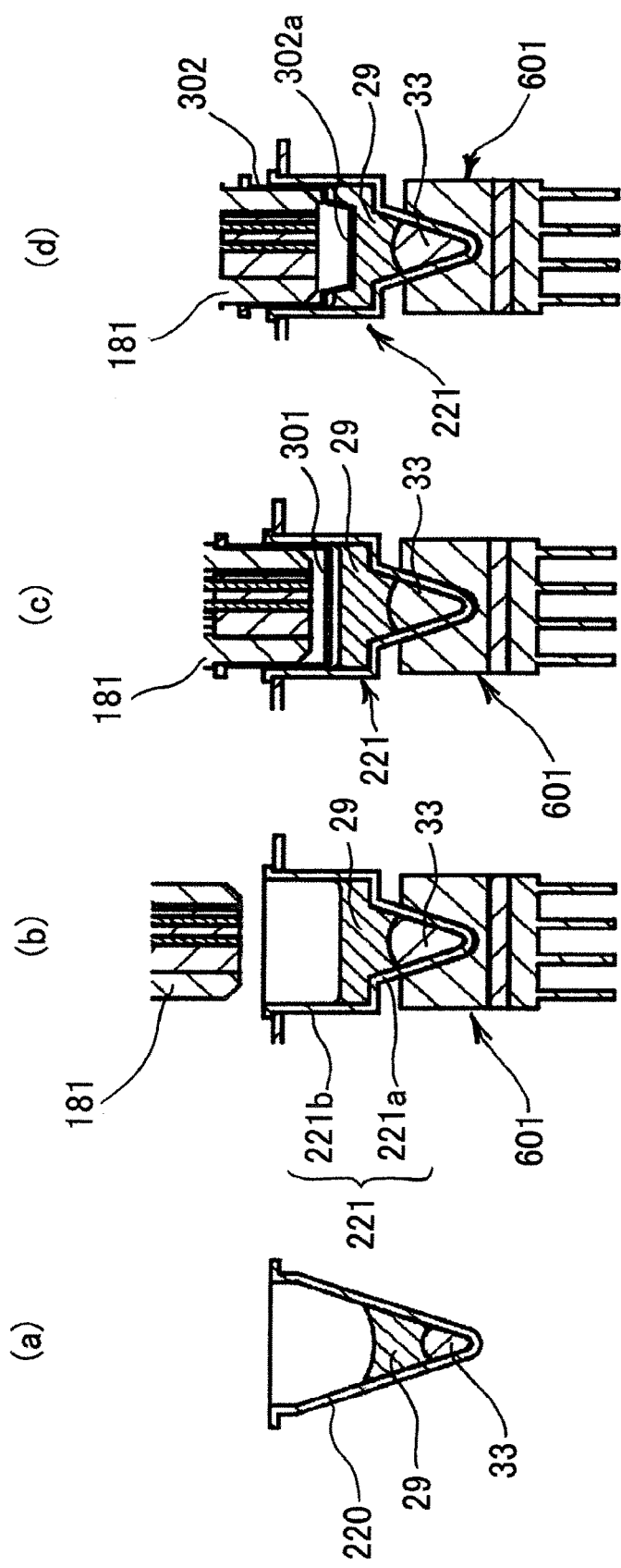
[Fig. 7]

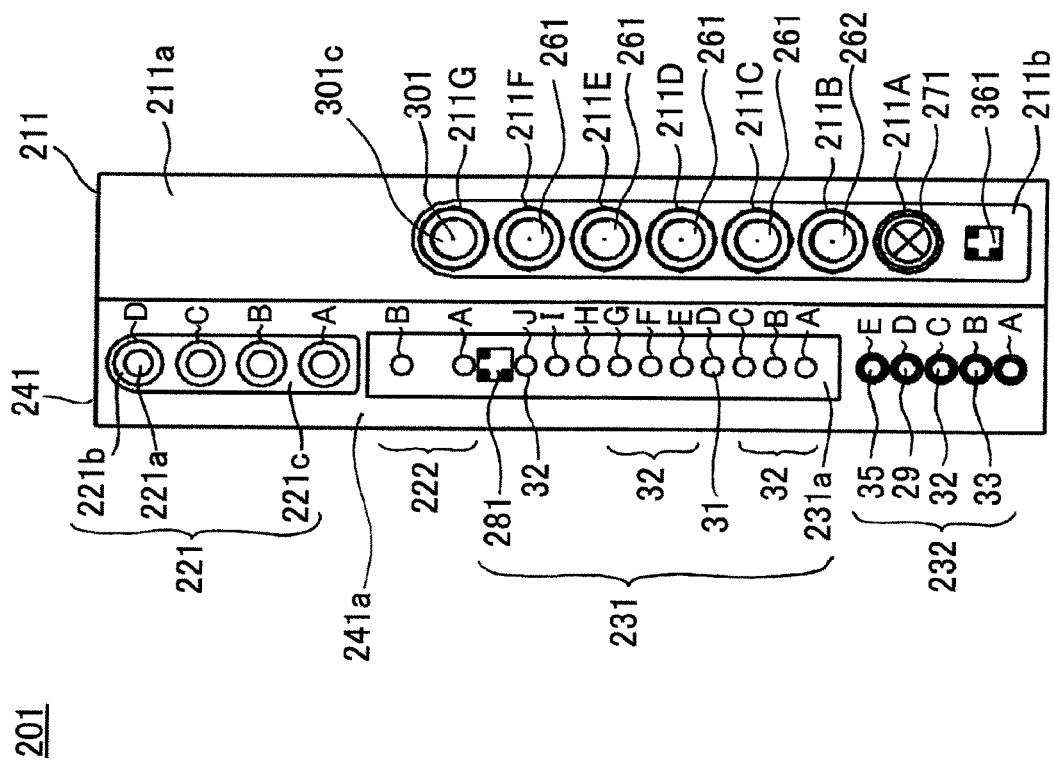
[Fig. 8]

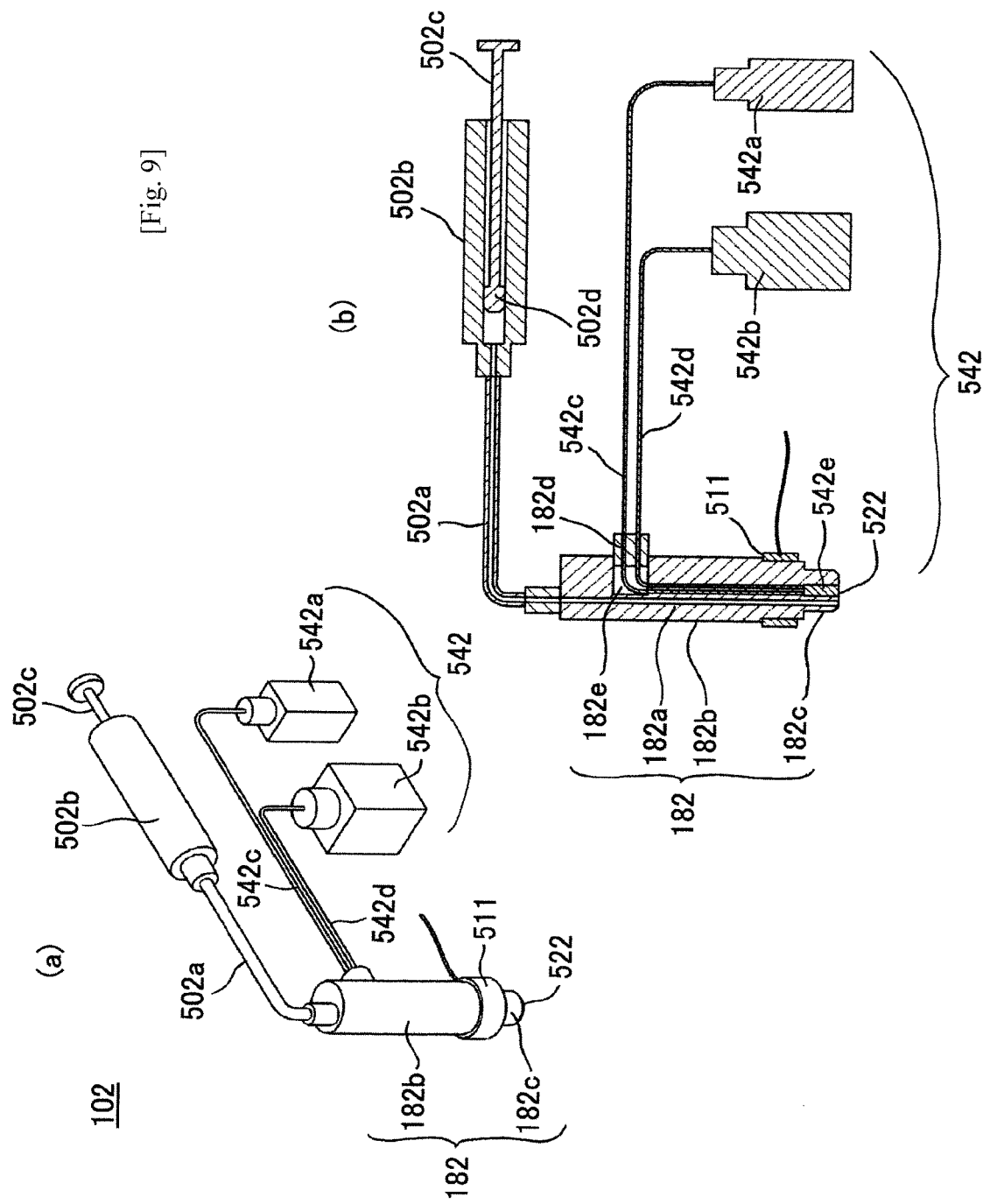

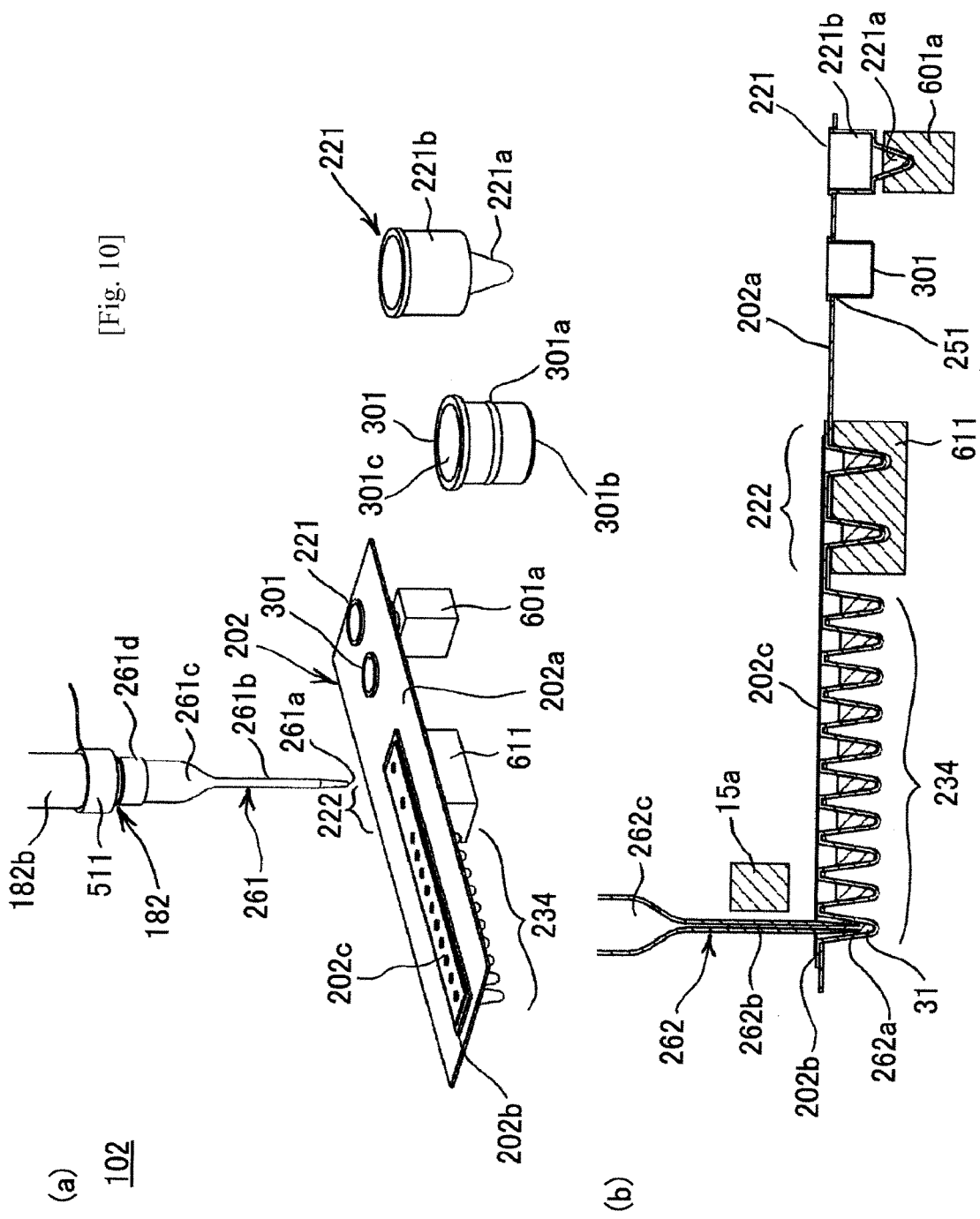

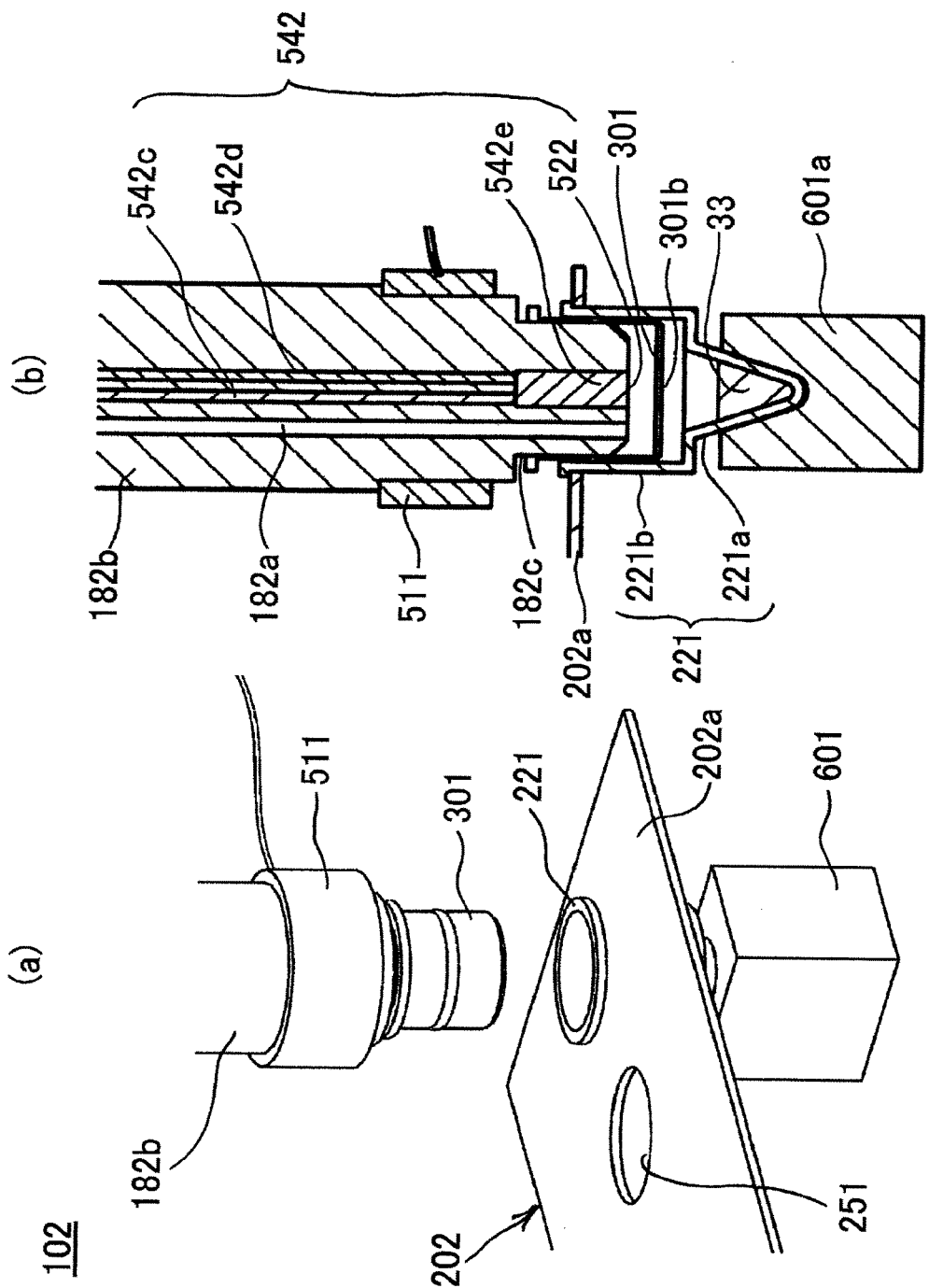
[Fig. 11]

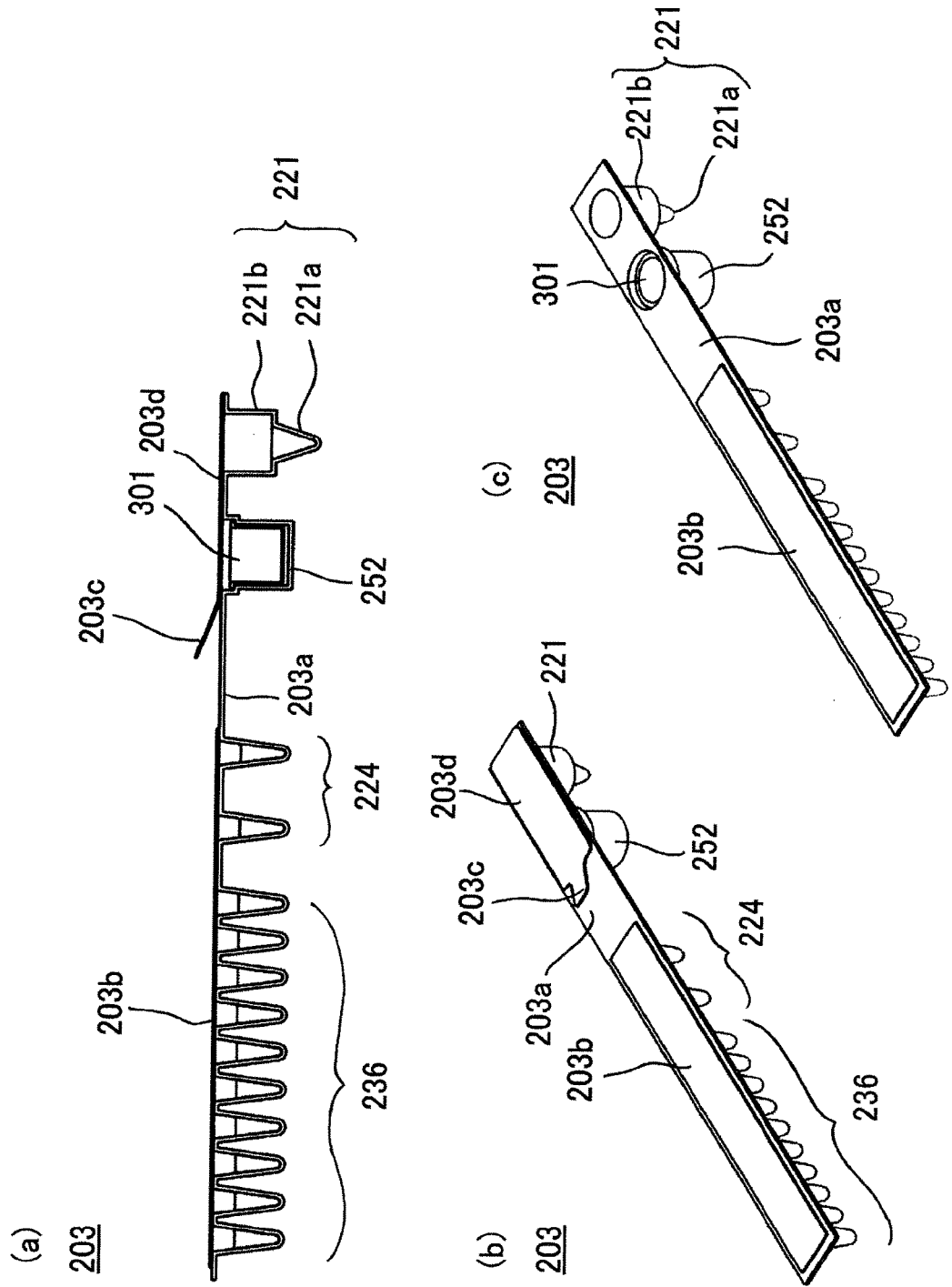
[Fig. 12]

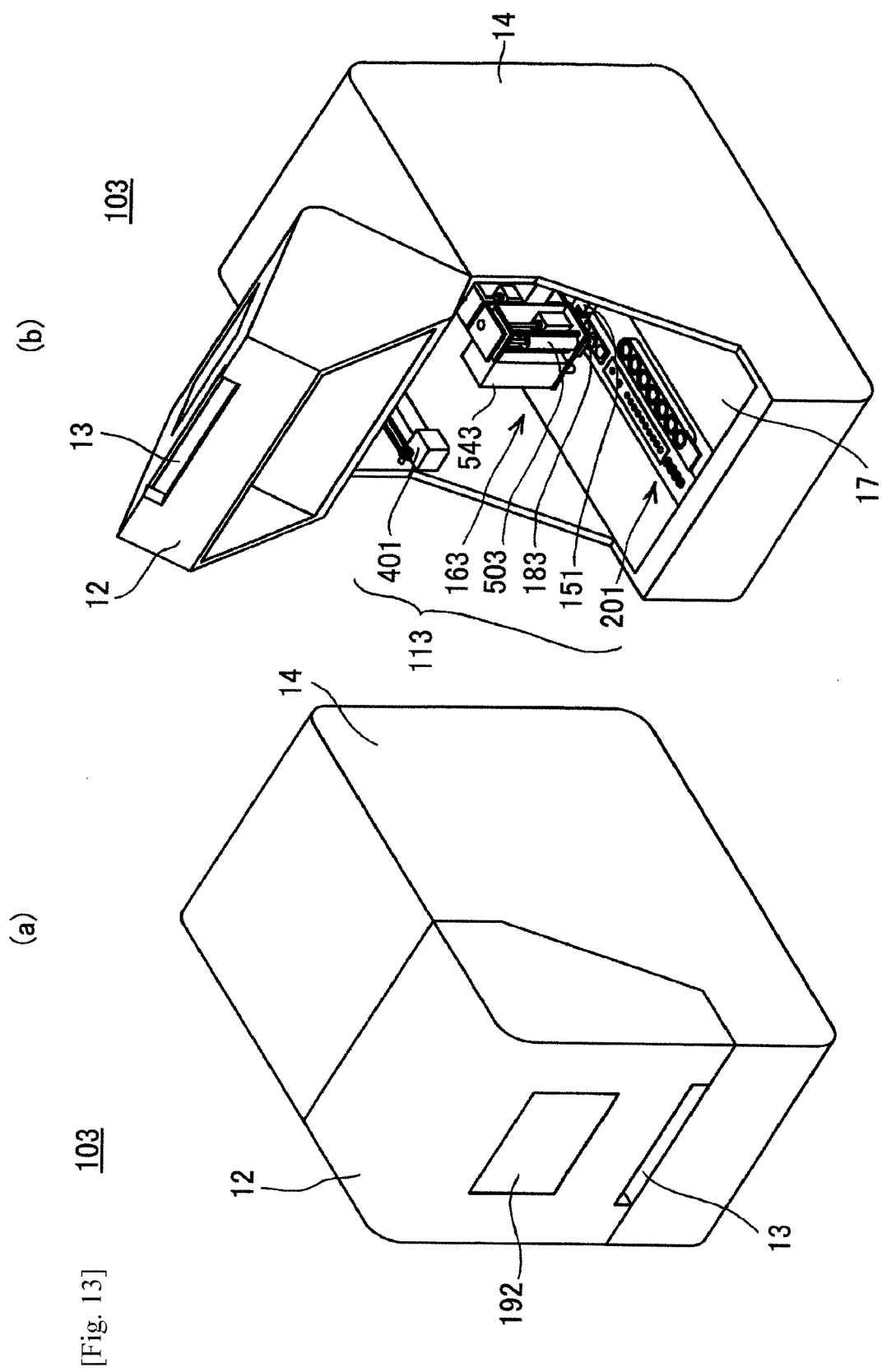

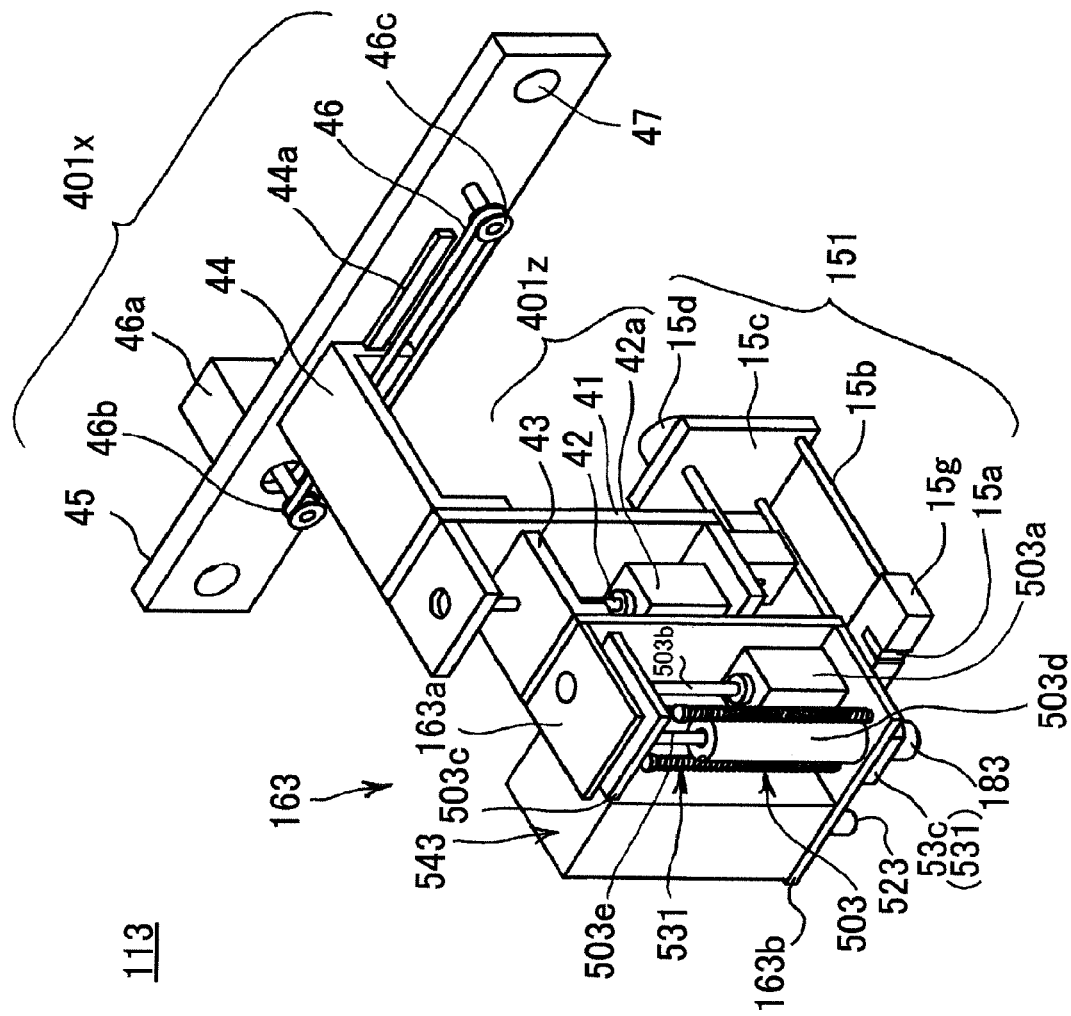
[Fig. 14]

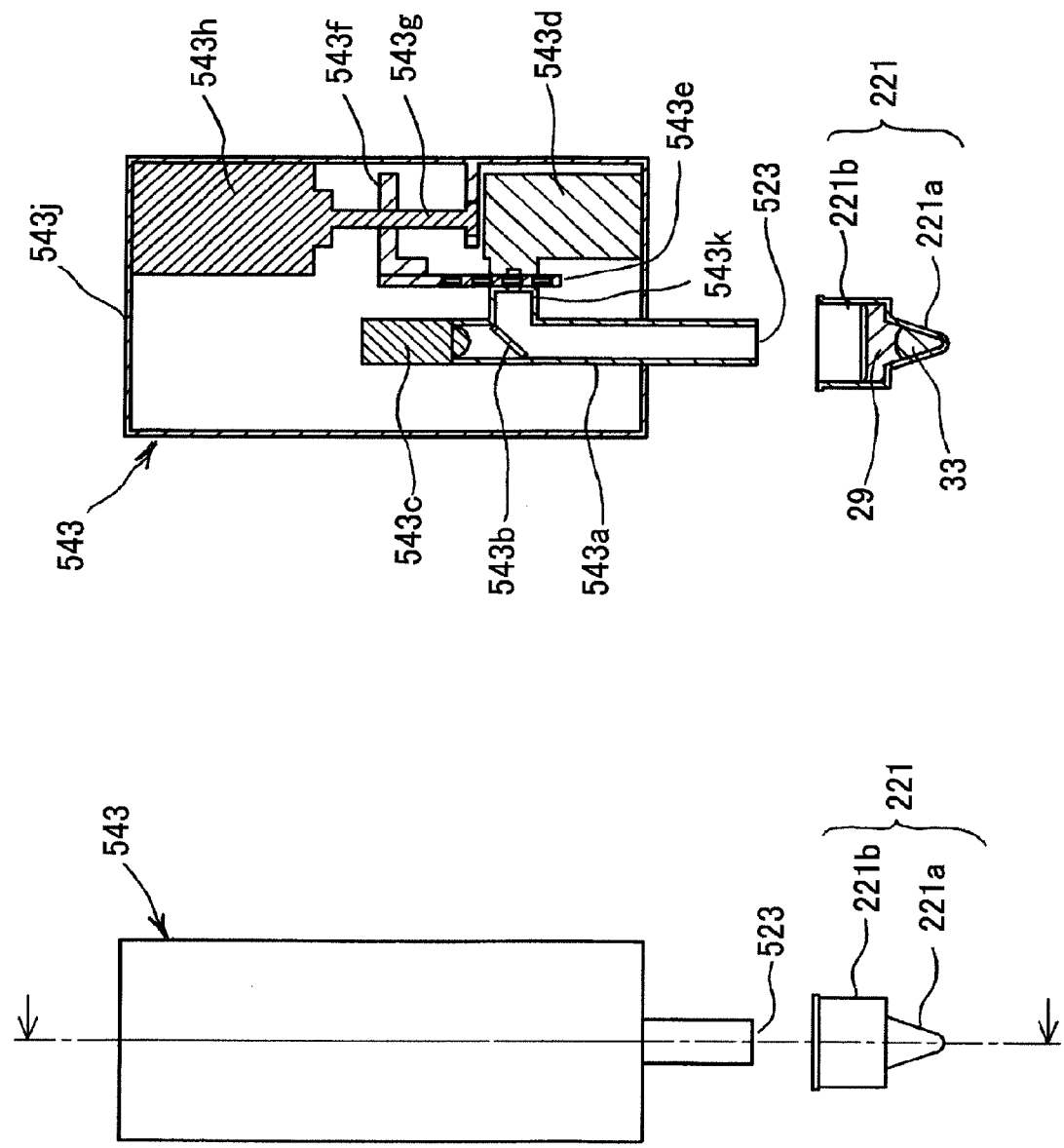
[Fig. 15]

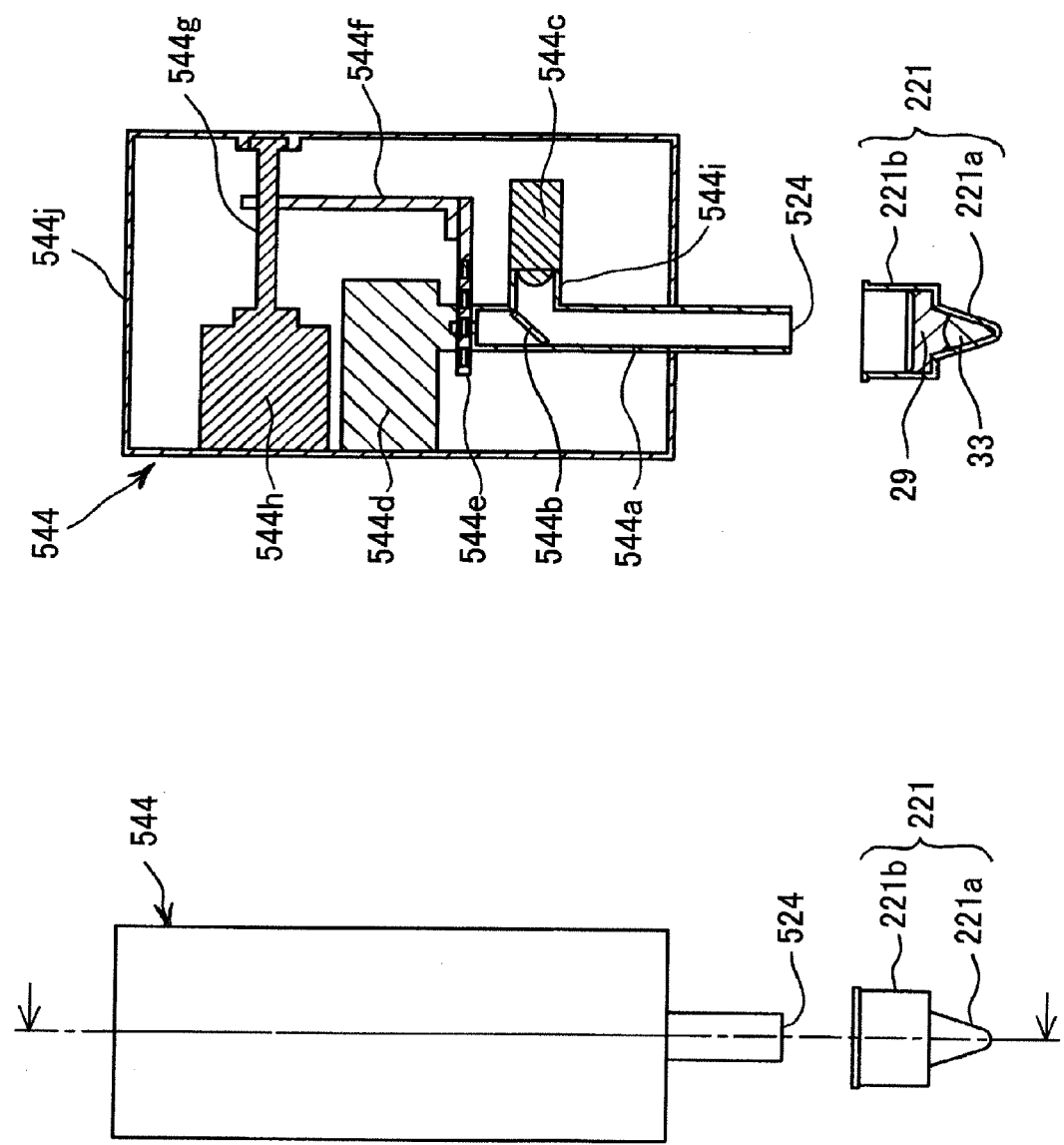
[Fig. 16]

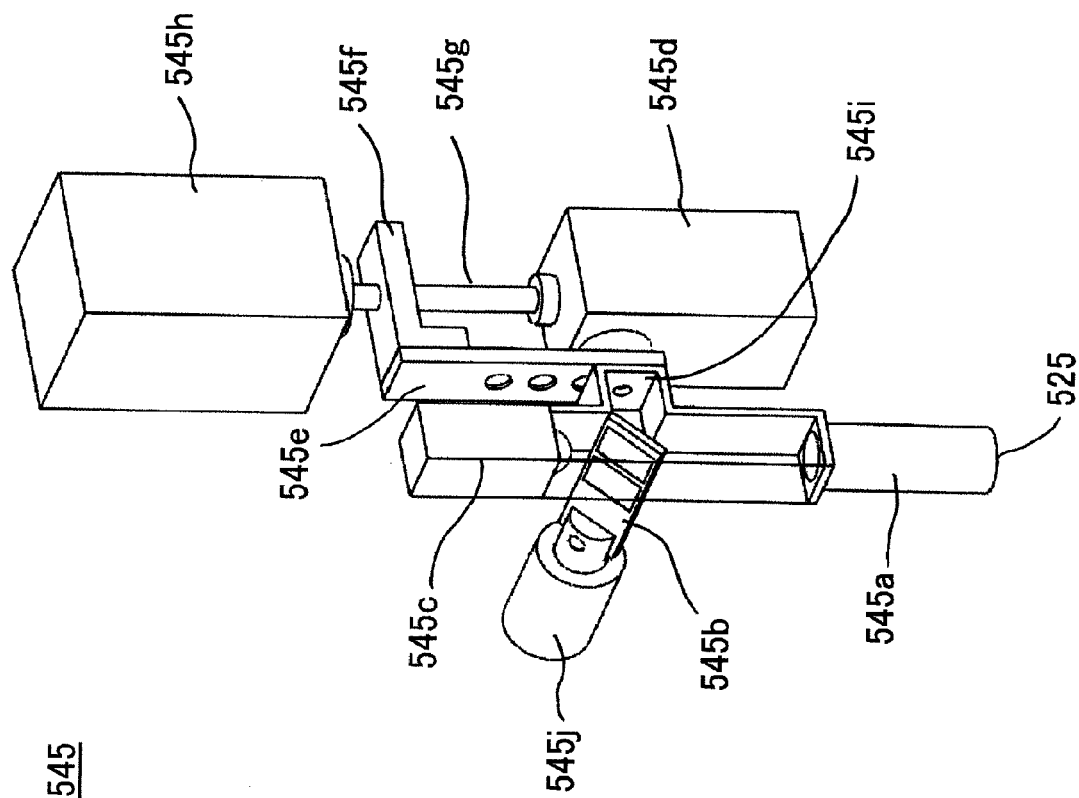
[Fig. 17]

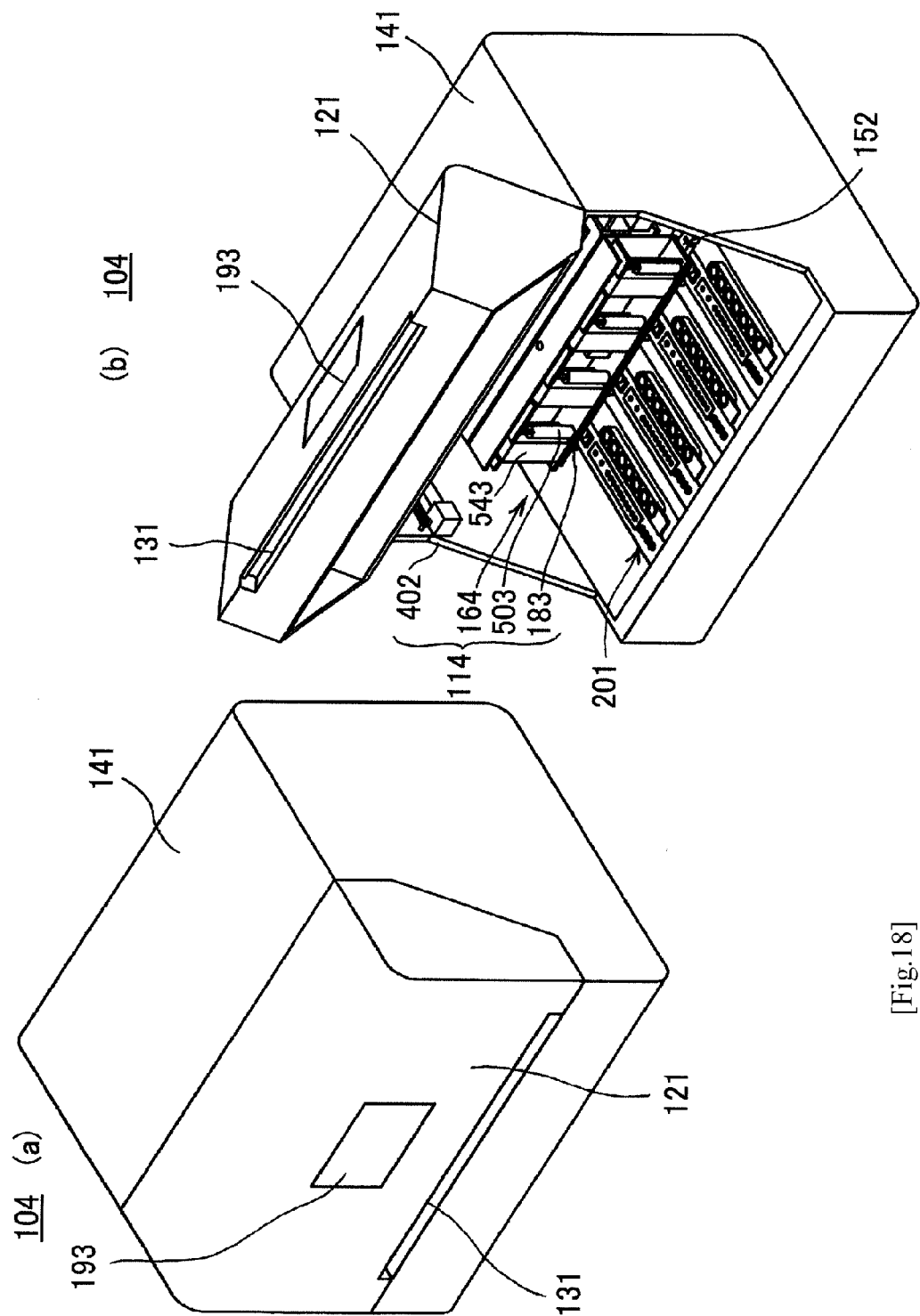
[Fig.18]

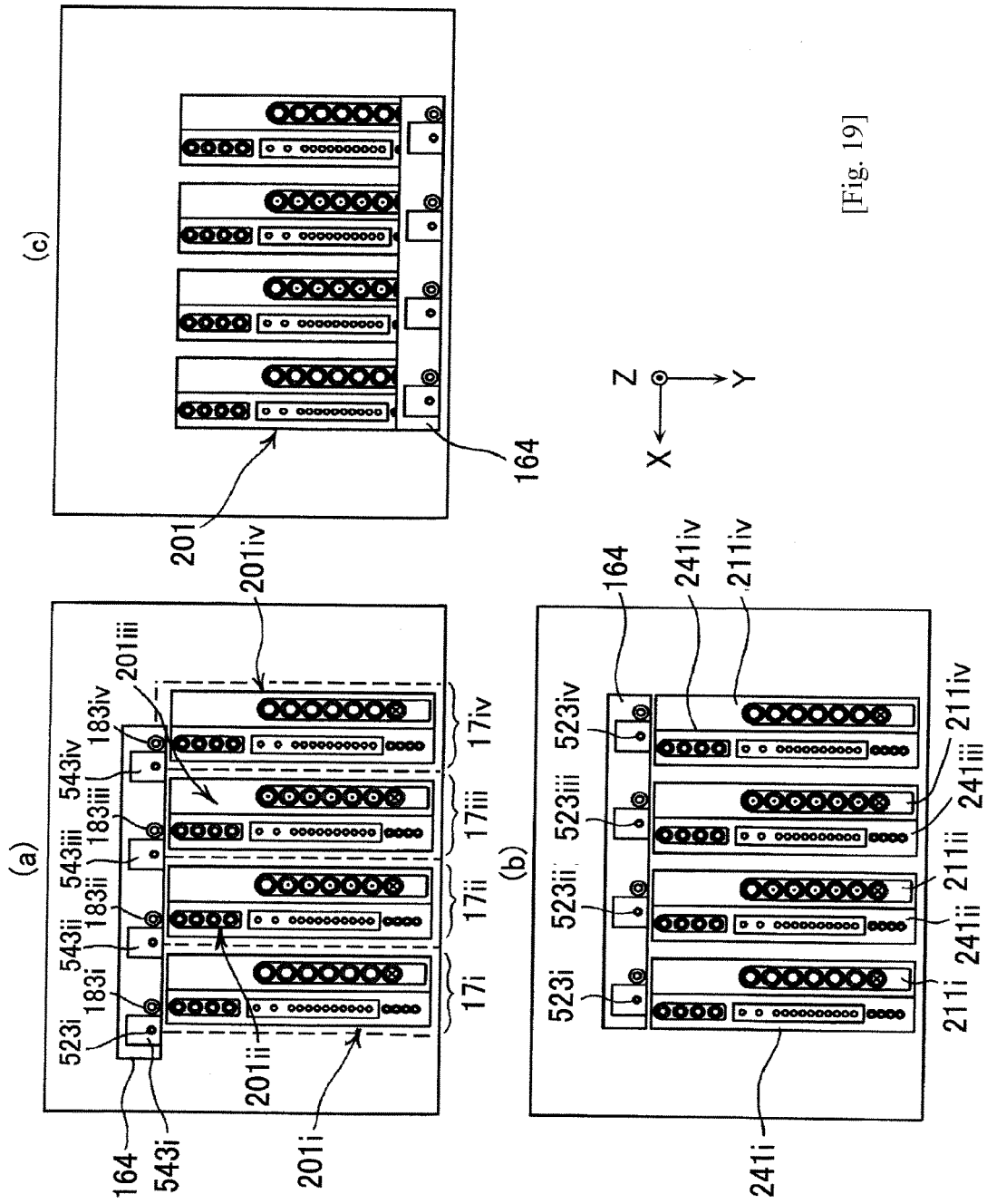
[Fig. 19]

AUTOMATED NUCLEIC ACID PROCESSOR AND AUTOMATED NUCLEIC ACID PROCESSING METHOD USING MULTI FUNCTION DISPENSING UNIT

CROSS REFERENCE

This application is a division of U.S. application Ser. No. 13/879,069, which is a national stage entry of international application number PCT/JP2011/073697, filed Oct. 14, 2011, which claims priority to Japanese patent application number 2010-233057, filed Oct. 15, 2010, the disclosures of which are incorporated herein by reference.

TECHNICAL FIELD

The present invention relates to an automated nucleic acid processor and an automated nucleic acid processing method using a multi function dispensing unit.

BACKGROUND ART

At the time amplification of nucleic acids (DNA, RNA, and the like) and the fragments thereof (oligonucleotides, nucleotides, and the like) is performed, in tests that require quantitativeness, such as the analysis of gene expression levels, it becomes necessary to perform the amplification such that the ratio of the relative amounts of the respective nucleic acids can be known. Consequently, by using the real-time PCR method, and by using a device provided with a thermal cycler and a fluorescence spectrophotometer, analysis by electrophoresis is made unnecessary as a result of the generation process of the DNA amplification products in PCR being detected and analyzed in real time. Furthermore, as a DNA amplification method that performs amplification while maintaining the quantitativeness with respect to the ratio of the relative amounts of the DNA or RNA contained in the sample before amplification, the SPIA (Single Primer Isothermal Amplification) method is used. In the SPIA method, the linear DNA amplification method resulting from an isothermal reaction utilizing DNA/RNA chimera primer, DNA polymerase and RNaseH has become used.

The temperature control in such nucleic acid amplification houses a vessel formed from polypropylene or the like, that contains the necessary reagents, such as the aforementioned template DNA, primers, DNA polymerase, nucleotides, and reaction buffer solutions, within a block-shaped housing part of an isothermal device formed from a material such as aluminum, and by heating or cooling the metallic block-shaped housing part and waiting until the solution temperature becomes a uniform temperature distribution, it is made to perform heating or cooling isothermally or at a next temperature (Patent Documents 1, 2 and 3).

At that time, sealing of the vessel for performing the temperature control with a lid prevents the entry of contaminants from the exterior, prevents fluid leakage from the interior, and is particularly necessary in order to exclude the effect of the air and the air temperature as much as possible until the reaction mixture within the housing part is heated or cooled, and the solution temperature becomes a uniform temperature distribution.

Then, in the real-time PCR method and the like, which monitors the nucleic acids (DNA, RNA, and the like) that are amplified in real time by utilizing a fluorescent compound, it is necessary to observe the amplification during a temperature cycle. Consequently, with respect to a vessel sealed with a lid, it is necessary to open the lid in order to perform optical measurements, or to perform light measurements from the exterior through a transparent lid or side surface. However, the manual opening of the lid by a user is time-consuming, and becomes an obstacle toward the consistent automation of the processing. Furthermore, at the time the lid is resealed, there is a concern of contamination from making contact with the reaction mixture in the vessel interior. Moreover, at the time of the temperature control, even if the lid is attempted to be removed from the vessel, it is difficult to easily open the lid due to the lid becoming adhered to the vessel opening as a result of moisture, and there is a concern in that rapid processing can not be performed. At the time the lid is opened, there is also a concern of contamination occurring from the liquid attached to the inside of the lid dripping or splashing (Patent Document 4).

Furthermore, at the time of the temperature control, in a case where measurements of the interior of the vessel are performed from the exterior of the vessel, although there is a need to make the lid of the vessel transparent and to perform the measurements from the exterior, there is a concern of the interior of the lid becoming cloudy from condensation, and the measurements becoming difficult.

On the other hand, in order to perform nucleic acid amplification, as a precondition thereof, it becomes necessary to extract a small amount of nucleic acids from the sample and to perform processing of the nucleic acids as template DNA within the reaction vessel together with various reagents, primers, DNA polymerase, nucleotides, reaction buffers, and the like, manually or using various devices for example. Therefore, in the present state, researchers and technicians that are specialized with regard to nucleic acids are needed.

This situation is preventing the generalization of genetic analysis and the expansion of clinical applications in hospitals, and the like. Therefore, at the time of clinical use and the like, in order to prevent cross-contamination and to reduce user labor, and to easily perform from the extraction, the amplification, and further, by means of a measurement, the genetic analysis of nucleic acids, then in addition to the need for full automation which consistently automates steps from the extraction, the amplification, and further up to the measurement of nucleic acids, the miniaturization of the device, and the provision of an inexpensive, high-accuracy device are important.

PRIOR ART DOCUMENTS

Patent Documents

[Patent Document 1] Japanese Patent Publication No. 2622327
[Patent Document 2] Published Japanese translation No. 2000-511435 of PCT International Publication
[Patent Document 3] U.S. Pat. No. 5,958,349
[Patent Document 4] Japanese Unexamined Patent Publication No. 2002-10777

SUMMARY OF THE INVENTION

Problems to be Solved by the Invention

Therefore, the present invention is one that has been achieved in order to solve the problems mentioned above. A first object thereof is in providing an automated nucleic acid processor and an automated nucleic acid processing method using a multi function dispensing unit that consistently automates the processing of nucleic acids by utilizing a multi function dispensing unit, which at least includes processing from the extraction of the nucleic acids and the amplification of the nucleic acids, and which reduces user labor and can be rapidly, efficiently, and inexpensively manufactured and utilized without expanding the scale of the device.

A second object thereof is in providing an automated nucleic acid processor and an automated nucleic acid processing method using a multi function dispensing unit in which optical measurements with a high reliability are possible with respect to the solution within the reaction vessel in which amplification of the nucleic acids is performed.

A third object thereof is in providing an automated nucleic acid processor and an automated nucleic acid processing method using a multi function dispensing unit wherein, by making it possible to non-manually perform dispensing, temperature control and/or optical measurements with respect to the reaction vessel in which the amplification of the nucleic acids is performed, processing with a high reliability can be performed by preventing with certainty contaminations due to the entry of contaminants into the reaction vessel interior from the exterior, or fluid leakage from the reaction vessel for example.

Means for Solving the Problem

A first aspect of the invention is an automated nucleic acid processor using a multi function dispensing unit comprising: a nozzle head having a suction-discharge mechanism that performs the suction and the discharge of gases, and one or two or more nozzles that detachably mount dispensing tips, whereby the suction and discharge of liquids is possible by means of the suction-discharge mechanism; a container group having, at the very least, one or two or more liquid housing parts that house amplification solutions used for nucleic acid amplification and one or two or more reaction vessels; a transfer mechanism that makes an interval between the nozzles and the container group relatively movable; a temperature controller whereby temperature control of the interior of the reaction vessels for nucleic acid amplification is possible; a sealing liquid and/or sealing lids housed in predetermined vessels other than the reaction vessels of the container group that are transportable to the reaction vessels using the nozzles, which make the amplification solutions housed in the reaction vessels sealable within the reaction vessels; and a sealing control part that controls the suction-discharge mechanism and the transfer mechanism, or the transfer mechanism, such that the sealing liquid and/or the sealing lids seal the amplification solution within the reaction vessels when the housing of the amplification solution in the reaction vessels is completed.

In order to "detachably mount", it is preferable to provide a detaching mechanism that detaches dispensing tips from the nozzles, on the nozzle head or the stage on which the container is provided for example. In order to make the dispensing tips, and the like, mountable on the nozzles, they are housed in a tip housing part provided within the container in a state where the apertures of the dispensing tips for mounting to the nozzles are on the upper side for example. As a result of a vertical direction transfer mechanism of the transfer mechanism, the mounting can be performed by moving it in a direction that brings closer the interval between the nozzle and the tip housing part, and inserting the lower end of the nozzle into the interior of the aperture for mounting to the nozzle. Furthermore, in order to perform extraction of materials such as DNA from the sample, it is preferable to provide a magnetic force part on the nozzle head, whereby it is possible to apply and remove a magnetic force within the mounted dispensing tip.

Here, examples of the "detaching mechanism" include mechanisms that are provided with a plate on the nozzle head or a stage opened with holes with a diameter larger than the outer diameter of the nozzles but smaller than the thickest section of the dispensing tips, and that detach the mounted dispensing tips by relatively lowering or raising the plate along the axial direction of the nozzles, which penetrate the respective holes. The detaching is, in a case where the plate is provided on the nozzle head for example, performed by linking the plate to the driving mechanism of a piston sliding within a cylinder, which represents the suction-discharge mechanism. In a case where the plate is provided on the stage, it is performed by relatively moving the nozzles in the vertical direction with respect to the plate by means of the vertical transfer mechanism.

Since "the interval between the nozzles and the container is made relatively movable", there is a case where the container is fixed and the nozzles are moved, a case where the nozzles are fixed and the container is moved, and a case where both thereof are combined.

The container provided on the stage is preferably provided with: the reaction vessels; a plurality of liquid housing parts that house samples, liquids such as the reagents, for example, the amplification solutions used in nucleic acid amplification; and a tip housing part that houses tips, such as the dispensing tips or tips for punching that serve to punch a film provided such that it covers the aperture of the container. Furthermore, the container group includes: a microplate in which wells representing a plurality of liquid housing parts are arranged in a matrix form or a column (row) form, or a cartridge form vessel in which wells representing a plurality of liquid housing parts are arranged in a row form.

The "amplification solution" represents, in a case where amplification is performed by the PCR method for example, a template DNA solution which is the amplification subject, a primer solution, a DNA polymerase solution, a nucleotide solution, a reaction buffer solution, and the like. In a case where amplification is performed by the SPIA method, it represents a DNA/RNA chimera primer solution, a DNA polymerase solution, an RNaseH solution, and the like. Furthermore, generally, methods for performing real-time PCR using fluorescent reagents containing a fluorescent compound include the intercalation method, the hybridization method, and the LUX method. In the "intercalation method", a fluorescent compound such as SYBR (registered trademark) GREEN I or ethidium bromide, enters into double-stranded DNA at the time of the elongation reaction, and is a method in which the DNA amount is measured by irradiating an excitation light and utilizing the fluorescent light-emitting characteristics. Therefore, at the very least, the fluorescent material and a quencher that suppresses the light emission of the fluorescent material must be contained within the amplification solution. The "hybridization method" is a method that detects only a target PCR product by using a DNA probe labeled with a fluorescent material in addition to a PCR primer. That is to say, as a result of the DNA probe labeled by fluorescent light hybridizing with the target PCR product, the hybridized DNA (amount) thereof is detected. The "LUX method" is one that utilizes a property in which the fluorescent light signal of the fluorescent compound labeling the oligonucleotide is affected by the shape (such as a sequence, a single-strand, or a double-strand) of the oligonucleotide thereof. In actual real-time PCR, a PCR primer (LUX primer) that is labeled with one type of a fluorescent compound and a contrastingly unlabeled PCR primer are used to perform real-time PCR. The LUX primer thereof is labeled with a fluorescent compound in the vicinity of the 3'-terminus, and is designed such that it takes a hairpin structure in the interval between the 5'-terminus. When the LUX primer takes a hairpin structure, the quenching effect is resolved, and the fluorescent light signal becomes increased. By measuring this signal increase, the amount of the PCR product can be measured.

The nozzles or the dispensing tips mounted on the nozzles reach their vessels by means of the transfer mechanism, and at the vessels the suction and discharge of liquids, and the mounting or detaching of the tips, are possible.

Examples of the material of the vessels, which includes the reaction vessels, the lid, and the like, include resins such as polyethylene, polypropylene, polystyrene and acrylic, glass, metals, and metal compounds. The size of the vessels is, in addition to several μL to several 100 μL of liquid being storable, a size in which the ends of the dispensing tips are insertable for example. In the case of a cylindrical shape, the diameter of the size of one vessel is several mm to several 10 mm, and the depth is several mm to several 10 mm for example.

The "dispensing tips" comprise a thick diameter portion, a narrow diameter portion, and a transition portion that communicates between the thick diameter portion and the narrow diameter portion for example. The thick diameter portion has an aperture for mounting, into which the lower ends of the nozzles are inserted and the nozzles are mounted, and the narrow diameter portion has an end mouth portion in which liquids can flow in and flow out by means of the suction and discharge of gases by the suction-discharge mechanism. The dispensing tips and the nozzles are manufactured from organic substances such as resins of polypropylene, polystyrene, polyester, acrylic, and the like, and inorganic substances such as glass, ceramics, metals including stainless steel, metal compounds and semiconductors.

The "temperature controller" has a temperature source that is able to raise or lower the temperature within the reaction vessels which house the liquids that become subjected to temperature control, based on a signal from the exterior for example. The temperature source is one in which, for example, a Peltier element, a heater, a cooling device and the like is provided on a block-shaped member. In order to perform processing such as PCR, the temperature controller is preferably a thermal cycler using a Peltier element.

"Temperature control" represents, with respect to a liquid or a vessel that becomes the subject thereof, the maintaining of one or two or more set predetermined temperatures for set time periods, according to a specified sequence, and the execution at a specified frequency. The instructions to the temperature controller are carried out by sending a corresponding signal based on a program.

The "predetermined temperature" is a target temperature that an object, such as a liquid that becomes the subject, is to reach. In a case where nucleic acids, such as the DNA contained in the liquid, or oligonucleotides and the like, which represent fragments of nucleic acids, are amplified by the PCR method for example, the predetermined temperature that is set is a temperature cycle performed in the PCR method. That is to say, it represents temperatures that are respectively necessary for the denaturation, the annealing or the hybridization, and the elongation of DNA of approximately 94° C., a temperature in the interval from 50° C. to 60° C., approximately 50° C., and approximately 72° C. for example. On the other hand, in the case of the SPIA method, it becomes set at a fixed temperature, such as 55° C. for example.

Furthermore, the predetermined temperature includes a temperature for transition acceleration that shortens the transition time and keeps the single cycle time within a predetermined cycle time as a result of, in the case of a transition from a high-temperature predetermined temperature to a low-temperature predetermined temperature, performing cooling at a temperature for transition acceleration that is lower than these predetermined temperatures by means of the temperature controller, or, at the time of a transition from a low-temperature predetermined temperature to a high-temperature predetermined temperature, by performing heating at a temperature for transition acceleration that is even higher than these predetermined temperatures for example. The "predetermined time" is the time necessary for maintaining the respective temperatures, and although it depends on the type of the amplification method, the amount of reagents, and the liquids used in the PCR method, and the shape, the material, the size, the thickness, and the like, of the nozzles, a single cycle is, in total, from several seconds to several 10 seconds for example, and the processing time for the PCR method as a whole is of the order of approximately several minutes to several 10 minutes for example. The transition time is also included in the predetermined time.

The "suction-discharge mechanism" is for example a mechanism having a cylinder, a piston that slides within the cylinder, a nut portion joined to the piston, a ball screw in which the nut portion is threaded, and a motor that rotatingly drives the ball screw in both forward and reverse directions, or is a pump mechanism.

Examples of the "transfer mechanism" include mechanisms whereby the intervals between the reaction vessels, that is to say, between the stage on which the reaction vessels are provided and the nozzles are relatively movable in the axial direction of the nozzles and within the horizontal plane for example. Examples of the movement within the horizontal plane include a XY axis transfer mechanism that performs movement of the stage or the nozzles along the X axis and the Y axis, or a Y (X) axis transfer mechanism that performs movement along the Y axis or the X axis only. Examples of the movement of the nozzles in the axial direction include a vertical transfer mechanism provided on the nozzle head that moves the nozzles in the axial direction (Z axis direction) thereof. The actuators mentioned below are driven by means of this transfer mechanism such that they are linked with the nozzles.

The "sealing liquid and/or the sealing lids" represents one among a sealing liquid, sealing lids, or a sealing liquid and sealing lids. The sealing lids, for example, seal the reaction vessels by sealing the aperture of the reaction vessels, in which temperature control is performed, by fitting, and the like. The sealing liquid does not produce a reaction with the amplification solutions housed within the reaction vessels, and examples may include those using a liquid such as an oil-derived mineral oil with a smaller specific gravity than these solutions, or an oil form material that is a silicone oil and composed of straight-chain structure molecules in which the siloxane bonds are 2000 or less.

Performing the sealing using not only the sealing liquid but also using the sealing lids is preferable in order to not contaminate the periphery from the liquids within the reaction vessels overflowing at the time of measurement during temperature control, or following completion of temperature control or processing. The "predetermined housing part" represents a liquid housing part in the case of the sealing liquid, and represents a sealing lid housing part in the case of the sealing lids.

Here, the sealing control part, in order to perform sealing with the "sealing liquid, or the sealing liquid and the sealing lids", has a need to control the suction-discharge mechanism and the transfer mechanism, and in order to perform sealing with the "sealing lids", has a need to control the transfer mechanism.

In order to transport the sealing lids to the reaction vessels, there is a need for the sealing lids to be detachably mounted on the end portions of the nozzles by fitting, threading, friction, adsorption, and the like. On the other hand, since the suction-discharge mechanism of the nozzles is used in order to transport the amplification solutions following mounting of the dispensing tips on the nozzles, it becomes necessary to detach the dispensing tips in order to mount the sealing lids with the same nozzles.

In a case where the sealing liquid is used, at the time of temperature control, an oil film is formed and evaporation of the amplification solution is prevented. Furthermore, as a result of an insulating effect, condensation on the sealing lids is prevented, and the opening and closing of the sealing lids is simplified. Moreover, by preventing the inclusion of gases within the amplification solutions, a uniform temperature control can be performed. By using the sealing liquid, the sealing lids are made unnecessary at the time of temperature control, and air does not enter between the oil film and the amplification solution. Therefore a mechanism that seals between the liquid and the oil film during temperature control becomes unnecessary. Furthermore, since condensation does not occur between the oil film and the amplification solution, it is also not necessary to heat or shake the sealing lids, and the construction can be simplified. Even in a case where temperature control is performed by sealing with the sealing liquid, for the control of the amplification solution, it is preferable to perform sealing with the sealing lids following temperature control.

The "sealing control part" is composed of a computer (CPU) built into the automated nucleic acid processor, and a program that drives the computer. Sealing control is achieved by transmitting signals through a DA converter to the respective mechanisms and control parts that drive the nozzles and the transfer mechanism for example.

In a case where two or more nozzles are used, by respectively arranging two or more containers so as to correspond to the respective nozzles within two or more dedicated regions corresponding to the respective nozzles, in which a single nozzle enters and the other nozzles do not enter, and by setting the respective dedicated regions for each different sample, cross-contamination between samples can be prevented with certainty.

A second aspect of the invention is an automated nucleic acid processor using a multi function dispensing unit wherein the container group further comprises two or more liquid housing parts that house; a sample, a magnetic particle suspension in which magnetic particles that are able to capture nucleic acids or the fragments thereof, which represents the amplification subject, are suspended, and a solution for separating and extracting used for the separation or the extraction of the amplification subject, and in addition to further having a magnetic force part that is able to apply or remove a magnetic force within the dispensing tips mounted on the nozzles or the liquid housing parts provided in the container group, and which is able to adsorb the magnetic particles on an inner wall of the dispensing tips or the liquid housing parts, it further has an extraction control part that controls the suction-discharge mechanism, the transfer mechanism, and the magnetic force part, and separates and extracts the solution of the amplification subject from the sample and houses it within the liquid housing parts as a portion of the amplification solution.

Here, the "solution for separating and extracting" includes a dissolving solution that breaks down or dissolves the protein forming the cell walls and the like contained in the sample and discharges the nucleic acids or the fragments thereof to the outside of the bacteria or the cell, a buffer solution that simplifies the capture of the nucleic acids or the fragments thereof by the magnetic particles, and additionally, a solution that dissociates from the magnetic particles, the nucleic acids or the fragments of nucleic acids captured by the magnetic particles. In order to perform the separation of the nucleic acids or the fragments thereof, it is preferable to repeat the suction and the discharge of the mixed solution.

A third aspect of the invention is an automated nucleic acid processor using a multi function dispensing unit comprising: a nozzle head provided with a suction-discharge mechanism that performs the suction and the discharge of gases, and one or two or more nozzles that detachably mount dispensing tips and are able to perform the suction and the discharge of liquids by means of the suction-discharge mechanism; a container group that, at the very least, has one or two or more liquid housing parts that house amplification solutions used in nucleic acid amplification, one or two or more reaction vessels, two or more liquid housing parts that house a sample, a magnetic particle suspension in which magnetic particles that are able to capture nucleic acids or the fragments thereof which represents the amplification subject are suspended, and a solution for separating and extracting used for the separation or the extraction of the amplification subject, and two or more tip housing parts that mountably house one or two or more dispensing tips; a detaching mechanism whereby the dispensing tips are able to be detached from the nozzles; a transfer mechanism that makes an interval between the nozzles and the container group relatively movable; a temperature controller whereby temperature control for nucleic acid amplification within the reaction vessels is possible; a sealing liquid and/or sealing lids housed in predetermined housing parts other than the reaction vessels of the container group, which are transportable to the reaction vessels using the nozzles and are able to seal within the reaction vessels the amplification solutions housed in the reaction vessels; a magnetic force part that is able to apply and remove a magnetic field with respect to the interior of the dispensing tips mounted on the nozzles or the liquid housing parts provided in the container group, and is able to adsorb the magnetic particles on an inner wall of the dispensing tips or the liquid housing parts; an extraction control part that controls the suction-discharge mechanism, the transfer mechanism, the detaching mechanism, and the magnetic force part, mounts the dispensing tips on the nozzles, separatingly extracts a solution of the amplification subject from the sample and houses it within the liquid housing part as a portion of the amplification solution, and detaches the dispensing tips from the nozzles; and a sealing control part that, once the housing of the amplification solution into the reaction vessel is completed, controls the suction-discharge mechanism and the transfer mechanism, or the transfer mechanism, such that the sealing liquid and/or the sealing lid seal the amplification solution within the reaction vessel.

A fourth aspect of the invention is an automated nucleic acid processor using a multi function dispensing unit comprising a measuring part that is able to measure an optical state, including light emissions, colors, color changes, or light variations generated within the amplification solutions sealed within the reaction vessels by means of the sealing liquid and/or the sealing lids, one or two or more measuring ends that receive light based on the light emissions and the like and are provided on the nozzle head, and a measurement control part that the measurement is made possible by controlling the transfer mechanism such that the measuring ends are made to approach the reaction vessels following sealing of, or at the time of sealing of, the amplification solutions containing the amplification subjects in the reaction vessels.

Here, it is preferable to provide the measuring part with an excitation light irradiation portion that irradiates excitation light, and a fluorescent light receiving function. Examples of the location in which the measuring end is provided include: a case where the end surface of the nozzles is provided with a light receiving end, or a light receiving end and an irradiation end, which are end portions of the optical fibers provided on the measuring part, which represents the measuring end, and the measurement is performed from the upper side of the reaction vessels; a case where it is provided on the nozzle head outside of the nozzles and movable by means of the transfer mechanism, and the measurement is performed from the side surface of the reaction vessels, which has a transparency; and a case where the measurement is performed from the upper side through the sealing liquid and/or the sealing lid, which have a transparency. Furthermore, by using a plurality of types of light emitting compounds, colored compounds, color changing compounds, or light variation compounds and performing amplification processing in parallel under the same conditions on a plurality of types of amplification subjects in a single reaction vessel, it is possible to perform multiplex PCR amplification or multiplex real-time PCR on a plurality of types of amplification subjects by using a primer labeled with a plurality of types of light emitting compounds for example.

A fifth aspect of the invention is an automated nucleic acid processor using a multi function dispensing unit wherein the measuring end is provided on the nozzle head, the sealing liquid and/or the sealing lids have a transparency, and the measurement control part controls the transfer mechanism such that the optical state is measurable through the sealing liquid and/or the sealing lid which seal the amplification solutions within the reaction vessels, from an upper side thereof.

A sixth aspect of the invention is an automated nucleic acid processor using a multi function dispensing unit wherein the measuring part is provided with one or two or more optical fibers provided such that they pass through the interior of the nozzle and are able to receive or irradiate light through an end surface of the nozzle, to which an aperture of a flow piping connected to the suction-discharge mechanism and passing through the interior of the nozzle is provided, and the end surface corresponds to the measuring end.

In this case, the flow piping is connected to the suction-discharge mechanism via the piping. Furthermore, by providing the optical fibers on the exterior of the nozzle along a path direction that is different to the piping, the suction-discharge mechanism, and the unit for receiving light and the unit for irradiation, to which the optical fibers are connected, can be compactly formed and provided on the nozzle head.

By providing the optical fibers through the interior of the flow piping of the nozzle and occupying a portion of the region thereof, the construction of the end portion can be simplified by sharing without providing any exclusive holes to the end portion of the nozzle.

A seventh aspect of the invention is an automated nucleic acid processor using a multi function dispensing unit wherein a measuring end of the measuring part is provided on the nozzle head separated from an end portion of the nozzle by leaving a predetermined spacing and such that it is linked with the nozzle, and by approaching the aperture of the reaction vessels of the container group from the upper side, is able to receive light or irradiate light via the sealing liquid and/or the sealing lid.

Here, the "predetermined spacing" is defined such that on the stage of the multi function dispensing unit, the nozzle and the measuring end do not make contact with the housing parts in the container at the same time for example. By making the predetermined spacing large, and if the measuring end can be made a size in which light ray bundles can be incident and can be irradiated with respect to the entire area of the liquid surface of the section housing the amplification solution, processing with a high reliability can be performed from the amplification solutions. This requires an optical aperture of a size that approximately covers the surface of the section of the reaction vessel in which the amplification solutions are housed, to be provided.

In a case where a plurality of groups of nozzles and measuring parts are used, it is preferable to set the predetermined spacing such that a measuring end corresponding to a given nozzle does not enter into the exclusive region mentioned below corresponding to another nozzle. Furthermore, it is preferable for the measuring end to have an optical aperture that is determined according to the size and the shape of the aperture of the section of the reaction vessels of the container housing the amplification solutions. In the measuring part mentioned above, by making the wavelengths or the wavelength ranges of a plurality of types of fluorescent light or excitation light selectable, it is possible to house a variety of fluorescent compounds or light emitting compounds.

An eighth aspect of the invention is an automated nucleic acid processor using a multi function dispensing unit in which the sealing control part controls the suction-discharge mechanism and the transfer mechanism such that, following mounting of the dispensing tips on the nozzles, by aspirating a predetermined amount of the sealing liquid from the predetermined housing part of the container group with the dispensing tips and discharging the sealing liquid into the reaction vessels in which the amplification solutions are housed, transports the sealing liquid and seals the amplification solutions within the reaction vessels.

A ninth aspect of the invention is an automated nucleic acid processor using a multi function dispensing unit, wherein the temperature controllable reaction vessels have a narrow piping part or a thin piping part in which the amplification solution is housed, and a wide-mouthed piping part communicated with the narrow piping part or the thin piping part and provided on the upper side of the narrow piping part or the thin piping part, which has a wider aperture than the aperture of the narrow piping part or the thin piping part and which houses the sealing liquid, and the sealing control part performs control based on an amount of the amplification solution such that an amount of the sealing liquid that reaches the wide-mouthed piping part is housed in the reaction vessel.

Here, the reason for the configuration of this reaction vessel is that in a case where measurements are performed from the upper side of the reaction vessel, which is sealed with the sealing liquid, if the spreading of the sealing liquid is small, there is a concern of the surface forming a curved surface with a large curvature as a result of the surface tension between the inner walls of the reaction vessel, and the measurements becoming difficult to perform due to the occurrence of light scattering. On the other hand, in order to make uniform temperature control of the amplification solution possible, there is a need to house it within a vessel that is as compact as possible. Therefore, the shapes of the section that houses the sealing liquid and the section that houses the amplification solution, employ shapes that are each suitable as mentioned above.

A tenth aspect of the invention is an automated nucleic acid processor using a multi function dispensing unit, wherein the sealing lids have a fitting portion that is mountable by fitting to an end portion of the nozzles, and have a detaching mechanism whereby the sealing lids and the dispensing tips are detached from the nozzles, and the sealing control part controls the suction-discharge mechanism, the transfer mechanism, and the detaching mechanism such that, following mounting of the dispensing tips on the nozzles and housing the amplification solutions in the reaction vessels, the dispensing tips are detached from the nozzles, the sealing lids are mounted on the nozzles, and the amplification solutions are sealed within the reaction vessels. Here, the sealing lids are housed with the fitting portion facing upwards, such that they are mountable by lowering the end portion of the nozzles.

An eleventh aspect of the invention is an automated nucleic acid processor using a multi function dispensing unit, wherein the container group has the sealing liquid and sealing lids, the sealing lids have a fitting portion that is mountable by fitting to an end portion of the nozzles, and there is provided a detaching mechanism whereby the sealing lids and the dispensing tips are detached from the nozzles, and the sealing control part controls the transfer mechanism and the detaching mechanism such that, when the housing of the amplification solutions within the reaction vessels is completed and following transport of the sealing liquid to the predetermined housing parts, the dispensing tips are detached from the nozzles, and the sealing lids are mounted on the nozzles and transported to the reaction vessels, so as to seal the apertures thereof.

Consequently, since the sealing liquid covers the amplification solutions, owing to the thermal insulation properties, air does not expand as a result of the temperature control, and not only can the dispersion of the amplification solutions be prevented, but the condensation on the sealing lids, which have a transparency, can be prevented. Therefore measurements with a high reliability can be performed from the outside.

The relationship between the sealing liquid housed within the reaction vessels and the sealing lids mounted on the reaction vessels includes not only a case when they are separated, but also a case where the sealing liquid and the sealing lid are making contact, or a case where a portion of the sealing lid is immersed within the sealing liquid. In the case where a portion of the sealing lid is immersed within the sealing liquid, by performing measurements through the section thereof that is immersed, measurements in which the air layer from the exterior of the reaction vessels is excluded can be performed.

A twelfth aspect of the invention is an automated nucleic acid processor using a multi function dispensing unit wherein, in a case where the sealing lids block the apertures of the reaction vessels, the sealing control part controls the suction-discharge mechanism or the transfer mechanism, and presses or shakes the sealing lids.

The pressing or the shaking is performed by means of the transfer mechanism, which moves the nozzles along the Z axis for example. Alternatively, in a case where the suction-discharge mechanism has; a cylinder communicated with the nozzles, a piston that slides within the cylinder, and a piston driving mechanism that drives the piston, it is performed by means of one or two or more actuators provided on the nozzle head and linked with the piston. The actuators are provided separately to the sealing lids for example, and have a shape such as a rod shape, cylinder shape, or a cone shape, and the lower end portions of the members are able to make contact with the sealing lids.

A thirteenth aspect of the invention is an automated nucleic acid processor using a multi function dispensing unit wherein, a heating portion is provided on an end portion of the nozzles, that heats the sealing lids, and the sealing control part, in a case where the sealing liquid is not housed within the reaction vessels, controls the heating portion such that the sealing lids are heated following the sealing of the apertures of the reaction vessels by means of the sealing lids. Here, the heating of the sealing lids by means of the heating portion is performed for preventing condensation at the time of temperature control of the reaction vessels sealed with the sealing lids.

A fourteenth aspect of the invention is an automated nucleic acid processor using a multi function dispensing unit wherein: the container group comprises one or two or more series of housing parts in which; a liquid housing part group having a plurality of vessels that house liquids or are able to house liquids formed in a single row form, and a housing parts for instruments group having a plurality of housing parts that house or are able to house instruments used by mounting on the nozzles formed in a single row form, are arranged in parallel; the liquid housing part group at the very least has one or two more of the reaction vessels that are temperature controllable by means of the temperature controller, a solution for separating and extracting used in the separation and extraction of samples, nucleic acids, and the fragments thereof, and a housing parts group for reagents and the like that houses or is able to house beforehand a magnetic particle suspension and an amplification solution used in the amplification of nucleic acids or the fragments thereof; the housing parts for instruments group at the very least houses or are able to house one or two or more dispensing tips that are mountable on the nozzle, and tips for punching that perform punching of a film for pre-packing in a state mountable on the nozzle, and the sealing liquid is housed in the liquid housing part group and/or the sealing lids are housed in the housing parts for instruments group.

The combination of the liquid housing part group formed in a single row form and the housing parts for instruments group formed in a single row form has the individual number of liquid housing parts and housing parts for instruments used to complete a single process of a single sample, or to complete the processing of a single sample by combining another liquid housing part group of a single row form and housing parts for instruments group formed in a single row form.

The "instruments" are instruments used by mounting on, or by being supported by, the nozzles of the multi function dispensing unit, and additionally include; solid state built-in tips used by mounting on the nozzles, wherein a predetermined biological material is provided fixed or able to be fixed in the interior such that it is identifiable from the exterior, or test paper for inspection used by being supported by the nozzle, or rod shaped instruments for pressing the sealing lids used by mounting on the nozzles, and so forth. Here, the "housing of instruments" does not necessarily require a wall portion that covers the housed instruments, and includes cases such as those in which the instruments are retained by fitting in holes.

The liquid housing part group of the container has an identification data display portion that displays identification data that identifies the liquid housing part group, the housing parts for instruments group has an identification data display portion that displays identification data that identifies the housing parts for instruments group, and the multi function dispensing unit has an identification data reader that reads the identification data displayed on the identification data display portions, and it is preferable that in the nucleic acid processing, the control portions are instructed based on these identification data.

Here, the "identification data" comprises "sample information" and "inspection information" for example. The sample information represents the information necessary for identifying or managing the sample, including the attributes of the sample, such as the patient, the animal, the food, the soil, the polluted water, or the like, from which the sample was collected, and includes the name, the age, the sex, and the ID number of the patient, the sales location of the food, and the collection location and the collection date and time of the soil, or the physical properties of the collected sample, including the classification of the blood, the urine, the faces, the bodily fluid, the cells, or the like, of the patient, the classification of the food, the classification of the soil, or the classification of the polluted water for example. Examples of the information that manages the samples include the collector and the collection date of the sample thereof, the contact person for the sample, and the inspection date of the sample thereof for example.

The "inspection information" represents information showing the content of the inspection performed with respect to the sample, and can include inspection items such as infectious diseases (identification of influenza, foot-and-mouth disease of livestock, and the like), autoimmune diseases (collagen diseases, DNA antibodies), various genetic information (SNPs, base sequence determination for example), genetic testing, or the types of reagents utilized in the inspection, the production lot number of the reagents, the calibration curves for the reagents, or the type and the structure of the instruments for testing for example. The identification data is displayed by a handwritten case, a printed case, a case where it is a barcode, or by a QR (registered trademark) code (a matrix form two-dimensional code) for example.

The "identification data reader" represents a digital camera for example, and the photographed image data can be easily uploaded into the memory of a computer using a USB cord, or the like. Therefore, input operations in which the information is uploaded by an operator using the keyboard of a computer become unnecessary. Furthermore, the data is easily transmitted, processed, or duplicated and applied to a variety of cases. The transmission of the image data may be performed by providing a communication portion on the sample inspection device for example.

A fifteenth aspect of the invention is an automated nucleic acid processor using a multi function dispensing unit having: a suction-discharge mechanism that performs the suction and the discharge of gases; a nozzle head provided with two or more nozzles that detachably mount dispensing tips; a container group provided with at least one or two or more liquid housing parts that house amplification solutions used in nucleic acid amplification, which are arranged within two or more respective exclusive regions corresponding to nozzles into which a single nozzle enters and the other nozzles do not enter, a liquid housing part that houses a magnetic particle suspension in which magnetic particles that are able to capture nucleic acids or the fragments thereof are suspended, a liquid housing part that houses a sample, two or more liquid housing parts that house a solution for separating and extracting used in the separation and the extraction of nucleic acids and the fragments thereof, reaction vessels, and a sealing liquid and/or sealing lids transportable to the reaction vessels by using the nozzles and that are able to seal within the reaction vessels the amplification solutions housed in the reaction vessels; a transfer mechanism that makes an interval between the nozzles and the container group relatively moveable, and restricts movement of the nozzles to within the respective exclusive regions; a magnetic force part whereby the magnetic particles are adsorbable on an inner wall of the dispensing tips mounted on the nozzles; a temperature controller provided on the respective container groups whereby temperature control within the reaction vessels for nucleic acid amplification is possible; a measuring part whereby an optical state, including light emissions, colors, color changes, or light variations generated within the amplification solutions sealed within the reaction vessels by means of the sealing liquid and/or the sealing lids, is measurable, which is provided on the nozzle head with respective measuring ends that receive the light based on the light emissions and the like, corresponding to the respective exclusive regions; and a nucleic acid processing controller that, at the very least, by controlling the suction-discharge mechanism, the transfer mechanism, the temperature controller, or the magnetic force part, instructs separation and extraction of nucleic acids and the fragments thereof from the sample using the magnetic particle suspension and the solution for separating and extracting by means of the dispensing tips, mixing of the amplification solutions containing the extracted nucleic acids or the fragments thereof by means of the dispensing tip, sealing of the amplification solutions in the reaction vessels by means of the sealing liquid and/or the sealing lids, temperature control, and the measurement of the optical state by approaching the measuring end to the sealed reaction vessel.

The nucleic acid processing controller is provided with the extraction control part, the sealing control part, and the measurement control part, and by further controlling the interval between these control parts, the extraction of the nucleic acids, the amplification of the nucleic acids, and the measurement of the nucleic acids can be consistently performed by utilizing the multi function dispensing unit. The sealing control part, the extraction control part, the measurement control part, and the nucleic acid processing controller are configured by a CPU built into the automated nucleic acid processor and a program that drives the CPU.

A sixteenth aspect of the invention is an automated nucleic acid processing method utilizing a multi function dispensing unit, the method comprising: transporting amplification solutions from one or two or more liquid housing parts provided in a container group that house amplification solutions used in nucleic acid amplification to temperature controlled reaction vessels for nucleic acid amplification provided in the container group using; the dispensing tips detachably mounted on the nozzles, whereby the suction and the discharge of liquids is possible by means of a suction-discharge mechanism that performs the suction and the discharge of gases, a suction-discharge mechanism which performs the suction and the discharge of the gases, and a transfer mechanism that makes an interval between and the nozzles and the container group relatively movable, and by means of the suction-discharge mechanism and the transfer mechanism, or the transfer mechanism, transporting sealing liquid and/or sealing lids from predetermined housing parts other than the reaction vessels of the container group into the reaction vessels using the nozzles, sealing the amplification solutions within the reaction vessels, and performing temperature control of the interior of the reaction vessels.

There is a case where the sealing within the reaction vessels by means of the sealing lids is performed both at the time of temperature control and following completion of temperature control in order to seal the sealing liquid and the amplification solutions within the reaction vessel such that they are sealed and do not leak out.

A seventeenth aspect of the invention is an automated nucleic acid processing method utilizing a multi function dispensing unit wherein the container group is further provided with: two or more liquid housing parts that house a sample, a magnetic particle solution in which magnetic particles that are able to capture the nucleic acids or the fragments thereof, which represent the amplification subject, are suspended, and a solution for separating and extracting used for the separation and the extraction of the amplification subject; and one or two or more tip housing parts that house dispensing tips, and the method comprises: using the dispensing tips and mixing and reacting the sample and a dissolving solution representing the solution for separating and extracting that breaks down or dissolves protein contained in the sample; capturing the amplification subject on the magnetic particles by mixing and reacting the reaction mixture and the magnetic particle solution; separating the magnetic particles by using a magnetic force part provided on the nozzle head and applying a magnetic field within the dispensing tips or the liquid housing parts to thereby adsorb the magnetic particles on an inner wall of the dispensing tips or the liquid housing parts; making contact between a dissociation solution representing an other separation and extraction solution housed in the container; dissociating the amplification subject from the magnetic particles; and housing a solution of the amplification subject in the liquid housing part as a portion of the amplification solution.

An eighteenth aspect of the invention is an automated nucleic acid processing method utilizing a multi function dispensing unit comprising, following sealing or at the time of sealing of the amplification solutions in the reaction vessels, making the measuring end to approach the reaction vessels by using the transfer mechanism, and receiving the light within the amplification solutions, and measuring an optical state including light emissions, colors, color changes, or light variations generated within the amplification solutions sealed within the reaction vessels with the sealing liquid and/or the sealing lid.

A nineteenth aspect of the invention is an automated nucleic acid processing method utilizing a multi function dispensing unit wherein the measurement step comprises positioning the measuring end provided on the nozzle head on an upper side of the sealing liquid and/or the sealing lid that is sealing the amplification solution within the reaction vessel by using the transfer mechanism, and performing the measurement of the interior of the amplification solution through the sealing liquid and/or the sealing lid, which have a transparency.

A twentieth aspect of the invention is an automated nucleic acid processing method utilizing a multi function dispensing unit wherein the measurement step comprises moving the measuring end which is provided on the nozzle head such that it is separated from the end portion of the nozzles by leaving a predetermined spacing and is linked with the nozzles, and making incident or irradiating via the sealing liquid and/or the sealing lid, light ray bundles corresponding to the width and shape of an aperture of a section of the reaction vessels housing the amplification solutions.

A twenty-first aspect of the invention is an automated nucleic acid processing method utilizing a multi function dispensing unit wherein the sealing step comprises, following mounting of the dispensing tips on the nozzles, sealing the amplification solutions within the reaction vessels by using the dispensing tips, the suction-discharge mechanism, and the transfer mechanism to transport a predetermined amount of the sealing liquid from the predetermined housing part of the container group, and discharge it within the reaction vessels. Here, the "predetermined amount" is an amount that is able to cover the entire surface of the amplification solution, and is determined by the shape of the reaction vessels and the volume of the housed amplification solution.

A twenty-second aspect of the invention is an automated nucleic acid processing method utilizing a multi function dispensing unit wherein the sealing, following mounting of dispensing tips on nozzles and housing of the amplification solutions in reaction vessels, is performed by detaching the dispensing tips from the nozzles, mounting the sealing lids on the nozzles using a fitting portion of the sealing lids and transporting them to the reaction vessels, and blocking an aperture of the reaction vessels.

A twenty-third aspect of the invention is an automated nucleic acid processing method utilizing a multi function dispensing unit wherein the sealing, when the housing of the amplification solutions within the reaction vessels is completed, has a step for transporting a predetermined amount of the sealing liquid to the reaction vessels, and then detaching the dispensing tips from the nozzles, mounting the sealing lids on the nozzles, transporting to the reaction vessels, and fitting to the apertures thereof. Here, the "predetermined amount" is an amount that, in addition to being able to cover the entire surface of the amplification solution, is able to block the reaction vessels with the sealing lid for example. This amount is determined based on the shape of the reaction vessels, the volume of the housed amplification solution, and the shape of the sealing lid.

A twenty-fourth aspect of the invention is an automated nucleic acid processing method utilizing a multi function dispensing unit comprising a step for mounting the sealing lids on the nozzles, transporting to the reaction vessels, and blocking the apertures thereof, and in a state where the sealing lids are mounted on the nozzles, pressing or shaking by means of the nozzles or the suction-discharge mechanism.

A twenty-fifth aspect of the invention is a processing method for nucleic acid extraction and amplification, and the like, utilizing a multi function dispensing unit comprising, in a case where the sealing liquid is not housed within the reaction vessels, following blocking of the apertures of the reaction vessels with the sealing lids, heating the sealing lids by heating the end portion of the nozzles at the time of temperature control of the reaction vessels. Here, the heating of the sealing lids is performed in order to prevent condensation that occurs on the sealing lids.

A twenty-sixth aspect of the invention is an automated nucleic acid processing method utilizing a multi function dispensing unit, the method comprising: from a liquid housing part group housing a sample, a magnetic particle suspension, and a solution for separating and extracting used for the separation and the extraction of nucleic acids and fragments thereof, provided in a container group which with respect to the two or more nozzles provided on the nozzle head, is provided within respective exclusive regions in which a single nozzle enters and the other nozzles do not enter, using dispensing tips detachably mounted on the nozzles, a suction-discharge mechanism that performs suction and discharge of gases, and a transfer mechanism that, in addition to making an interval between the nozzles and the container group relatively movable, restricts the movement of the respective nozzles to within the exclusive regions; transporting the samples and the solutions for separating and extracting to the reaction vessels and mixing and reacting them; mixing and reacting the magnetic particle suspension; capturing on the magnetic particles the nucleic acids or the fragments thereof obtained from the sample; separating the magnetic particles by applying a magnetic field within the dispensing tips or the liquid housing parts by means of a magnetic force part provided on the nozzle head and adsorbing them on the inner wall thereof; dissociating the nucleic acids and the fragments thereof by contacting the separated magnetic particles and a dissociation liquid; housing and mixing the dissociated nucleic acids or the fragments thereof as a portion of the amplification solutions in a temperature controllable reaction vessel by means of the suction-discharge mechanism and the transfer mechanism; sealing the amplification solutions in the reaction vessels with sealing liquid and/or sealing lids housed in the container group by means of the suction-discharge mechanism and the transfer mechanism, or the transfer mechanism; performing temperature control of the sealed amplification solutions by using the temperature controller; and measuring an optical state, including light emissions, colors, color changes, or light variations generated within the amplification solutions sealed within the reaction vessel by means of the sealing liquid and/or the sealing lids, by making a measuring end of a measuring part approach the sealed reaction vessels.

Effects of the Invention

According to the first aspect of the invention or the sixteenth aspect of the invention, in a case where the amplification solutions containing the nucleic acids or the fragments thereof have been housed in the temperature controllable reaction vessels, by controlling the sealing liquid and/or the sealing lid and utilizing an inherent dispensing function of the suction-discharge mechanism and the transfer mechanism such that the amplification solutions are sealed within the reaction vessels, the dispensing device is made multifunctional by providing an amplification solution sealing function to the device. Consequently, for the amplification processing of nucleic acids, which requires a high precision, it is made possible for the amplification processing to be performed without a user touching the solutions to be introduced to the reaction vessels, the housing parts in which the solutions are to be housed, the reaction vessels themselves, the attachments of the reaction vessels, and the like. Therefore, without expanding the device scale, the manufacturing costs are reduced, and automated processing of nucleic acids with a high reliability that can prevent cross-contaminations with certainty can be performed.

According to the second aspect of the invention or the seventeenth aspect of the invention, by also performing the separation and the extraction from the sample of the nucleic acids or the fragments thereof, which represents the amplification subject, using a dispensing function that is inherently provided to the multi function dispensing unit, the operation efficiency of nucleic acid amplification processing of the device is increased, and the series of processes from the separation and the extraction of the nucleic acids from the sample to the amplification can be consistently performed using the same device function, and consecutively without interruptions. Therefore, the expansion of the device scale is prevented, and in addition to the flow of the processing becoming consecutive and smooth, and the series of processes being able to be rapidly and efficiently performed, an inexpensive device can be provided.

According to the third aspect of the invention, in addition to providing a detaching mechanism, by housing the dispensing tips in a state where they are mountable on the nozzles, it becomes possible to perform sealing by utilizing an inherent mechanism for dispensing and detaching the dispensing tips from the nozzles, to which the dispensing tips are automatically mounted, and mounting the sealing lids. In addition, dispensing tips (tips for separating) that are to be used in the separation and the extraction of the amplification subjects from the samples, which have a comparatively large capacity, are detached, and as well as cross-contamination being prevented by mounting comparatively small dispensing tips that have a capacity that is appropriate for the amplification processing of the extracted amplification subjects, the steps from the separation and extraction of the amplification subjects from the samples, to the amplification can be more smoothly performed.

According to the fourth aspect of the invention and the eighteenth aspect of the invention, by providing measuring ends on the nozzle head, the processing based on nucleic acid amplification, and also the measurement of the amplification solution sealed by the sealing liquid and/or the sealing lid, becomes possible by utilizing the transfer mechanism used in an inherent dispensing function, and by controlling the transfer mechanism, and quantitative PCR measurements, such as real-time PCR, is made possible. According to the present invention, a measurement function that measures the optical state within the amplification solution, which becomes a sealed state by means of a sealing function, is provided by utilizing the transfer mechanism of the dispensing device, thus making it more multifunctional, and as a result, the consistency of the processing related to nucleic acids, and the like, is increased without expanding the device scale, and the production costs can be reduced.

According to the fifth aspect of the invention or the nineteenth aspect of the invention, the sealing liquid and/or the sealing lids have a transparency, and the measuring end can perform measurements of the optical state within the amplification solution with certainty via the sealing liquid and/or the sealing lids with the same positional relationship as a case where dispensing is performed, in which it is positioned on the upper side of the apertures of the reaction vessels. Therefore the control is simple and can be smoothly combined with dispensing processing, and the like.

According to the sixth aspect of the invention, the end surfaces of the nozzles are made measuring ends by using optical fibers, which represent the measuring part, passing through the interior of the nozzles. Therefore, even after the apertures of the reaction vessels are blocked with the sealing liquid and/or the sealing lids, the measurement can be subsequently performed at the nozzle positions thereof or by returning to the nozzle positions thereof again. Hence the operation efficiency is high. Furthermore, since the measuring ends can perform measurements with the same positional relationship as a case where dispensing is performed, in which the nozzles are positioned on the upper side of the apertures of the reaction vessels, the control is more simple, and the flow of processing is natural since it can be smoothly combined with dispensing processing, and the like.

According to the seventh aspect of the invention and the twentieth aspect of the invention, the measuring end is provided on the nozzle head separated from the nozzles by leaving a predetermined spacing from the nozzles. Therefore the control is simple since movement control utilizing the transfer mechanism can be performed with approximately the same positional relationship with the nozzles at the time dispensing is performed. Moreover, compared to a case in which measuring ends are provided on the nozzles, the measuring end can be provided regardless of the structure of the nozzles. Therefore the optical aperture of the measuring end, based on the size and the shape of the aperture of the section of the reaction vessels in which the amplification solutions are housed, is able to obtain a signal of a sufficient amount of light from the amplification solutions, and measurements with certainty and accuracy can be performed.

According to the eighth aspect of the invention or the twenty-first aspect of the invention, the amplification solutions housed in the reaction vessels are sealed using a sealing liquid. Therefore, the sealing can be performed with the same controls as for normal dispensing processing of liquids using the suction-discharge mechanism and the transfer mechanism. Hence dispensing processing, and the like, can be smoothly combined, and the control is simple. Furthermore, in a case where a sealing liquid is used, a liquid layer, such as a liquid film, is formed and the evaporation of the reaction solution is prevented. Moreover, as a result of a heat insulation effect, condensation on the solid lids and the measuring ends provided on the nozzle end surfaces to which it is fitted, is prevented, and in addition to making the opening and closing of the solid lids simple, it makes the measurements clear. Moreover, by preventing the inclusion of gases within the amplification solutions, a uniform temperature control can be performed. By using a sealing liquid, the solid lids are made unnecessary at the time of temperature control, and air does not enter into the interval between the oil film or the liquid film of the sealing liquid and the amplification solutions. Therefore a mechanism that seals the interval between the amplification solution and the liquid film (oil film) of the sealing liquid during temperature control, such as a pressing mechanism, becomes unnecessary. Furthermore, since condensation does not occur in the interval between the oil film and the amplification solutions, there is no need to perform shaking, and the like, of the oil film and the construction can be made simple. Moreover, in a case where a sealing liquid is used, the transparency is generally higher than a case where sealing lids are used, and it is possible to perform clear measurements. Even in a case where sealing is performed with just the sealing liquid, it is preferable to perform sealing with the sealing lids following temperature control.

According to the ninth aspect of the invention, the amplification solutions, which have a large relative density, have a small cross-sectional area at the narrow piping part or the thin piping part on the lower side, and the sealing liquids, which have a small relative density, can be housed such that the liquid surface area or the cross-sectional area at the wide-mouthed piping part on the upper side becomes large. Consequently, the effect of surface tension from the inner wall of the vessel on the sealing liquids is made small, and the optical state, including light emissions, colors, color changes, or light variations within the amplification solutions can be measured through the sealing liquids with an accuracy having a high reliability. It is preferable for the measuring ends to have an aperture on the upper side of the narrow piping part or the thin piping part that corresponds to the cross-sectional area thereof.

According to the tenth aspect of the invention and the twenty-second aspect of the invention, by making possible the mounting of the dispensing tips and the detaching thereof, the mounting of the sealing lids on the nozzles utilizing the transfer mechanism and the transport to the reaction vessels, and the sealing of the amplification solutions within the reaction vessels, from the housing of the amplification solutions within the reaction vessels to the sealing and the temperature control can be realized by the same controls as the dispensing processing by means of controlling the transfer mechanism and the suction-discharge mechanism and transfer mechanism, and consistent automated nucleic acid processing that is smooth and consecutive with respect to dispensing, sealing, and temperature control, can be realized without enlarging the device scale. Furthermore, following completion of amplification processing, since the reaction mixtures are sealed with the sealing lids, cross-contamination from fluid leakage of the amplification solutions can be prevented with certainty.

According to the eleventh aspect of the invention to the twenty-third aspect of the invention, by performing sealing of the amplification solutions by combining the two types of a sealing liquid and a sealing lid, the air layer between the sealing liquid and the sealing lid is excluded, or the expansion of the air layer is prevented, and as a result of a heat insulation effect of the sealing liquid, condensation on the sealing lid is prevented, and measurements with reliability can be performed. Therefore, the necessity of pressing or heating the sealing lids is excluded, and the construction can be simplified. Furthermore, since the reaction mixtures are also sealed within the reaction vessels with the sealing lids following completion of amplification processing, cross-contamination can be prevented with certainty.

According to the twelfth aspect of the invention or the twenty-fourth aspect of the invention, by pressing the sealing lids, the aperture of the reaction vessels can be blocked with certainty. Furthermore, by shaking the sealing lids, the sealed state between the apertures and the sealing lids can be rapidly and simply removed and released. Therefore, a high processing efficiency and reliability can be obtained.

According to the thirteenth aspect of the invention or the twenty-fifth aspect of the invention, by heating the sealing lids, even if a sealing liquid is not housed within the reaction vessels, condensation from the sealing lids on the aperture of the reaction vessels can be prevented. Furthermore, in the present invention, since heating is performed by heating the end portion of the nozzles, to which the sealing lids are mountable, heating can be performed with certainty in a state that is near the sealing lids.

According to the fourteenth aspect of the invention, a series of housing parts, in which a liquid housing part group comprising a plurality of housing parts that house liquids or are able to house liquids formed in a single row form, and a housing parts for instruments group comprising a plurality of housing parts that house or are able to house instruments that are used by mounting on the nozzle formed in at least a single row form, are arranged in parallel is provided. Therefore, for the processing of a single sample, the movement distance corresponding to the sum of the lengths of the rows in the longitudinal direction of the liquid housing part group and the housing parts for instruments group is shortened as a whole to the distance of the longer of either the liquid housing part group or the housing parts for instruments group, and only the movement of a fixed spacing in the width direction is added. Therefore, in addition to preventing the expansion of the device scale, except for the movement at the time of mounting or the time of detaching of instruments on the nozzles, the processing can be performed by movement on a straight line along the row. Therefore the control is simplified, and rapid processing with a high efficiency can be performed. Furthermore, by dividing the liquid housing part group which houses liquids, and the housing parts for instruments group which houses instruments such as the dispensing tip, the respective constructions are simplified, and the storage and the supply of the liquid housing part group and the housing parts for instruments group to the storage case is simplified.

According to the fifteenth aspect of the invention or the twenty-sixth aspect of the invention, two or more nozzles are used and exclusive regions provided for each nozzle into which the nozzles do not mutually enter are set, and it becomes possible to perform within the respective exclusive regions the steps from the extraction, and the amplification, to the measurement of nucleic acids or the fragments thereof simultaneously, consistently, and on a plurality of types of samples in parallel in the same device. Hence the processing efficiency is high, and processing with a high reliability that is rapid and without cross-contamination can be performed. Furthermore, the device scale is reduced, and it becomes possible for it to be provided inexpensively.

BRIEF DESCRIPTION OF THE DRAWINGS

FIG. 2 is a perspective view showing a first embodiment of the automated nucleic acid processor using a multi function dispensing unit shown in FIG. 1.

FIG. 3 is a side view and a perspective view showing enlarged, the nozzle head shown in FIG. 2.

FIG. 4 is a perspective view showing enlarged, the nozzle head and the transfer mechanism of the multi function dispensing unit shown in FIG. 2.

FIG. 5 is a perspective view showing a nozzle of the device shown in FIG. 2 to FIG. 4, a partially enlarged view, and a perspective view showing it partially cut away.

FIG. 6 is a cross-sectional view showing the state at the time of real-time PCR, in which the reaction vessel is sealed by mounting a sealing lid on the nozzle shown in FIG. 5.

FIG. 7 is a cross-sectional view showing various sealed states of the nozzle shown in FIG. 5, and the reaction vessel.

FIG. 8 is a plan view showing enlarged, the container provided on the stage of the multi function dispensing unit shown in FIG. 2.

FIG. 9 is a perspective view showing a second embodiment of the automated nucleic acid processor using a multi function dispensing unit show in FIG. 1.

FIG. 10 is a drawing in which a dispensing tip is mounted on the device according to the second embodiment shown in FIG. 9.

FIG. 11 is a cross-sectional view showing a state in which the reaction vessel is sealed by mounting a sealing lid on the nozzle shown in FIG. 9.

FIG. 12 is a plan view showing an example of a container according to a third embodiment of the device shown in FIG. 2.

FIG. 13 is a perspective view according to a fourth embodiment of the automated nucleic acid processor using a multi function dispensing unit shown in FIG. 1.

FIG. 14 is a perspective view showing enlarged, the nozzle head and the transfer mechanism of the multi function dispensing unit shown in FIG. 13.

FIG. 15 is a cross-sectional schematic view of a measuring unit of the measuring part shown in FIG. 13.

FIG. 16 is a cross-sectional schematic view of a measuring unit according to a fifth embodiment of the measuring part shown in FIG. 13.

FIG. 17 is a partially see-through perspective view of a measuring unit according to a sixth embodiment of the measuring part shown in FIG. 13.

FIG. 18 is a perspective view according to a seventh embodiment of the automated nucleic acid processor using a multi function dispensing unit shown in FIG. 1.

FIG. 19 is a plan view showing enlarged, the containers provided on the stage of the multi function dispensing unit shown in FIG. 18.

BEST MODE FOR CARRYING OUT THE INVENTION

Figure 1:
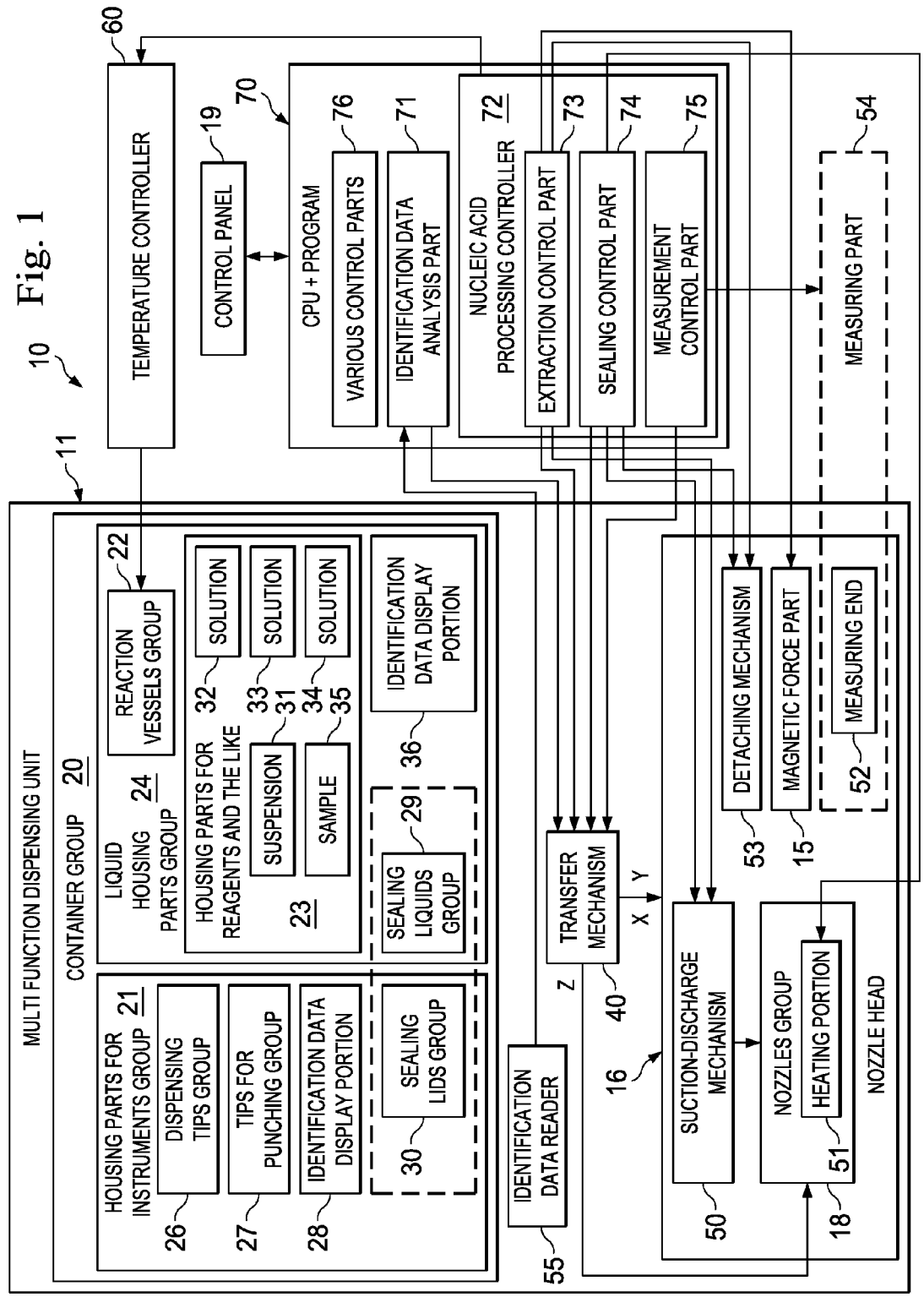
FIG. 1 is an overall block-diagram showing an automated nucleic acid processor using a multi function dispensing unit according to an embodiment of the present invention.

Next, an embodiment of the present invention is described with reference to the drawings. This embodiment is not to be interpreted as limiting the present invention unless particularly specified. Furthermore, in the embodiments, the same objects are denoted by the same reference symbol, and the descriptions are omitted.

FIG. 1 shows an automated nucleic acid processor using a multi function dispensing unit 10 according to an embodiment of the present invention.

The automated nucleic acid processor 10 broadly has: a multi function dispensing unit 11; a temperature controller 60; a measuring part 54; a CPU+program 70 composed of a CPU, a ROM, a RAM, various types of external memory, communication functions such as a LAN, a program stored in the ROM, and the like, provided for the multi function dispensing unit 11 and within the multi function dispensing unit 11 that performs various controls with respect to the temperature controller 60 and the measuring part 54; and a control panel 19 having a display portion such as a liquid crystal display, and an operation portion, such as operation keys or a touch panel.

The multi function dispensing unit 11 has: a nozzle head 16 having a suction-discharge mechanism 50 that performs the suction and the discharge of gases, and one or two or more mountable nozzles 18 to which dispensing tips 26, whereby the suction and the discharge of liquids is possible by means of the suction-discharge mechanism, are detachable; a container 20 having at least one or two or more liquid housing parts housing an amplification solution 33 used for nucleic acid amplification, and one or two or more reaction vessels 22; and a transfer mechanism 40 that makes the nozzles 18 movable with respect to the container 20. Furthermore, an identification data reader 55, such as a digital camera, is provided on the nozzle head 16 for reading the identification data displayed on the identification data display portions 28 and 36 of the container 20 mentioned below.

The temperature controller 60 is one having a temperature source that is able to raise or lower the temperature of the reaction vessels within the reaction vessel group 22 of the container 20, which house the liquids that become the subject of temperature control, based on the instructions from a nucleic acid processing controller 72 mentioned below that is provided for the CPU+program 70. The measuring part 54 is able to measure the optical state, including light emissions, colors, color changes, or light variations generated within the reaction vessels, and is one in which a measuring end 52 that receives the light based on the light emissions, and the like, is provided on the multi function dispensing unit 11.

The nozzle head 16 is movable with respect to the container 20 in the X axis direction and the Y axis direction by means of the transfer mechanism 40. The nozzle head 16 has: the nozzles 18 which are provided such that they are movable in the Z axis direction by means of the transfer mechanism 40; the suction-discharge mechanism 50; a detaching mechanism 53 that detaches from the nozzles 18 the various tips 26 and 27 mounted on the nozzles 18; a magnetic force part 15 that is able to apply and remove a magnetic force in the interior of the dispensing tips 26 mounted on the nozzles 18; and the measuring end 52.

The nozzles 18 have a heating portion 51 that heats the sealing lids 30 which seal the amplification solutions 33 housed within the reaction vessels 22 and have a transparency, and prevents condensation on the sealing lids 30.

The container 20 comprises one or two or more series of housing parts in which a liquid housing part group 24 comprising housing parts that house or are able to house liquids, and a housing parts for instruments group 21 composed of a plurality of housings parts that house or are able to house instruments used by mounting on the nozzles 18 of the multi function dispensing unit 11, are combined and made parallel. The liquid housing part group 24 has, in addition to the reaction vessel group 22: housing parts for reagents and the like 23 comprising at least one or two or more liquid housing parts that house a magnetic particle suspension 31, two or more liquid housing parts that house a solution for separating and extracting 32 used for the separation and extraction of nucleic acids and the fragments thereof, and two or more liquid housing parts that house an amplification solution 33 used for the amplification of nucleic acids; and a liquid housing part that houses a sealing liquid 29 for sealing within the reaction vessels 22 the amplification solutions 33 housed in the reaction vessels 22.

The housing parts for instruments group 21 has one or two or more dispensing tips 26, one or two or more tips for punching 27 for punching a film provided covering the aperture of the liquid housing part by being mounted on the nozzles 18, and sealing lids 30 for sealing the amplification solutions 33 housed within the reaction vessels 22.

At the liquid housing part group 24, the identification data that identifies the liquid housing part group is displayed on an identification data display portion 36, and at the housing parts for instruments group 21, the identification data that identifies the housing parts for instruments group 21 is displayed on an identification data display portion 28.

The CPU+program 70 has a nucleic acid processing controller 72 that performs instructions for a series of processes such as: the extraction and the amplification of nucleic acids and the fragments thereof, the sealing of the amplification solution, the measurement of the optical state including light emissions generated at the amplification solution, and the like, with respect to the temperature controller 60, the transfer mechanism 40, the detaching mechanism 53, the measuring part 54, the magnetic force part 15, the heating portion 51 or the suction-discharge mechanism 50; an identification data analysis part 71 that, with regard to the identification data displayed on the identification data display portions 28 and 36 of the container 20, analyzes the identification data read by the identification data reader 55; and various control parts 76 that control the suction-discharge mechanism 50, the transfer mechanism, and the like, based on signals from sensors, such as a pressure sensor provided on the multi function dispensing unit.

The nucleic acid processing controller 72 has: an extraction control part 73 that performs instructions for a series of processes regarding the extraction of nucleic acids and the fragments thereof with respect to the transfer mechanism 40, the suction-discharge mechanism 50 of the nozzle head 16, the detaching mechanism 53 and the magnetic force part 15; a sealing control part 74 that performs instructions regarding the sealing process of the amplification solutions with respect to the reaction vessels 22 with regard to the transfer mechanism 40 and the suction-discharge mechanism 50, or the detaching mechanism 53 and the heating portion 51; and a measurement control part 75 that performs instructions for measurements with respect to the measuring part 54.

FIG. 2 is a perspective view showing the automated nucleic acid processor using a multi function dispensing unit 101 according to a first embodiment.

FIG. 2A is a drawing showing an external view of the automated nucleic acid processor 101, which has: an enclosure 14 in which a multi function dispensing unit 111 corresponding to the multi function dispensing unit 11 is built into the interior; a door 12 that covers the aperture of the enclosure 14 such that it can be opened and closed; a control panel 191 corresponding to the control panel 19 having a liquid crystal display portion and operation keys provided on the door 12; and an indentation 13 for opening and closing of the door 12. Here, the size of the enclosure 14 is of the order of approximately 50 cm in depth, approximately 30 cm in width, and approximately 40 cm in height for example.

FIG. 2B is a drawing showing a state in which the door 12 is open. The interior of the enclosure 14 is provided with the multi function dispensing unit 111. The multi function dispensing unit 111 has: a nozzle head 161 corresponding to the nozzle head 16 provided with one or two or more (1 in this example) nozzles 181 corresponding to the nozzles 18, a suction-discharge mechanism 501 corresponding to the suction-discharge mechanism 50, and a magnetic force part 151 corresponding to the magnetic force part 15; a container 201 corresponding to the container 20 provided within a region in which the nozzles 181 on the stage 17 are movable and having a reaction vessel group in which the amplification of nucleic acids or the fragments thereof is performed; and a transfer mechanism 401 corresponding to the transfer mechanism 40 that makes the nozzles 181 movable in the X axis, Y axis, and Z axis directions with respect to the container 201.

FIG. 3A is a side view showing the nozzle head 161 and a Z axis transfer mechanism 401z that performs movement in the Z axis direction within the transfer mechanism 401, and FIG. 3B is a perspective view thereof.

The nozzle head 161 is one having: a head base portion 16a that is movable with respect to the container 201 in the X, Y, and Z axis directions and a bottom plate 16b joined thereto; nozzles 181 that are provided joined to the head base portion 16a which can mount dispensing tips 261 at an aperture for mounting 261d of the dispensing tips 261 (refer to FIG. 10); a suction-discharge mechanism 501 that is provided joined to the head base portion 16a that can perform the suction and the discharge of gases via the nozzles 181; a detaching mechanism 531 that is provided joined to the head base portion 16a that makes possible the detaching of the dispensing tips 261, and the like, mounted on the nozzles 181; and a measuring part 541 provided joined to the head base portion 16a having a measuring end 521 on the end face of the nozzles 181 that is able to measure the optical state, including light emissions, colors, color changes, or light variations generated within the reaction vessels, and which receives the light based on the light emissions, and the like.

The Z axis transfer mechanism 401z is a mechanism that makes the head base portion 16a and the members joined thereto movable in the Z axis direction with respect to an XY axis movable body 41 mentioned below, and has a Z axis motor 42a, a ball screw 42 that is rotatingly driven by the Z axis motor 42a, a Z axis drive plate 43 that threads with the ball screw 42 and is driven along the Z axis by means of the rotation of the ball screw, and an XY axis movable body 41 that is movable along the X axis direction and the Y axis direction by means of a X axis transfer mechanism 401x and a Y axis transfer mechanism 401y mentioned below that, in addition to mounting the Z axis motor 42a, axially supports the ball screw 42. The lower side of the XY axis movable body 41 is provided with a magnetic force part 151 having a magnet 15a provided such that it can approach and separate with respect to the tips for separating (dispensing tips) 262 mounted on the nozzles 181, and at the time the tips for separating 262 are positioned at a predetermined height position, it is possible to apply a magnetic force to the interior of the tips for separating 262.

The dispensing tips 261 have, as shown in FIG. 10A, a mouth portion 261a in which liquids can flow in and flow out by means of the suction-discharge mechanism 501, a narrow diameter piping 261b to which the mouth portion 261a is provided on the end, a thick diameter piping 261c joined with the narrow diameter piping 261b and formed thicker than the narrow diameter piping 261b, and an aperture for mounting 261d which is mounted on the nozzles 181 and is provided on the end of the thick diameter piping 261c. The tips for separating 262 have, as mentioned below, a larger volume than the dispensing tips 261 of approximately 1 mL.

The suction-discharge mechanism 501 has a P axis motor 501a, a ball screw 501b in which one end is joined with the P axis motor 501a and rotatingly driven by means of the P axis motor 501a, and the other end is axially supported by the head base portion 16a, a P axis drive plate 501c that is threaded with the ball screw 501b and is raised and lowered along the Z axis direction by means of the rotation of the ball screw 501b, a suction-discharge mechanism 501d that is communicated with the flow piping within the nozzles 181 via a vent piping 181d in which a piston is slidably provided in the interior, and a piston rod 501e, in which the piston is provided on one end, and the other end is joined with the P axis drive plate 501c.

The magnetic force part 151 has the magnet 15a provided such that it can approach and separate with respect to the narrow diameter piping 262b of a dispensing tip 262 that has moved to a predetermined height position, two parallel cantilever type rods 15b in which one end supports the magnet 15a and the other end is fixed, a support plate 15c on which the cantilever type rods 15b and a motor 15d are mounted, a ball screw 15e that, in addition to being rotatingly driven by means of the motor 15d, is axially supported by the support plate 15c, and a nut portion 15f that, in addition to threading with the ball screw 15e, is mounted on the lower side of the XY axis movable body 41 of the Z axis transfer mechanism 401z. In the drawing, reference symbol 551 represents a digital camera as the identification data reader 55 for reading the identification data displayed on the identification data display portions 281 and 361 mentioned below, of the container 201.

As clearly shown in FIG. 3B, the detaching mechanism 531 provided on the nozzle head 161 has: two inject pins 53a provided penetrating the bottom plate 16b joined with the head base portion 16a and whereby movement in the downward direction is possible by being pressed by means of the lowering of the P axis drive plate 501 of the suction-discharge mechanism 501; and a tip removal plate 53c that, in addition to being provided joined with the lower end of the inject pins 53a and on the lower side of the bottom plate 16b, is provided surrounding the nozzles 181 and movable along the axis direction, and piercingly provided with a hole 53b larger than the nozzles 181 but having a smaller inner radius than the largest outer radius of the respective tips 261, 262, and 271.

Furthermore, the detaching mechanism 531 is provided on the upper end of the inject pins 53a, and has head portions 53d that make contact with the P axis drive plate 501c, and springs 53e, in which one end is mounted on the bottom plate 16b and surrounds the inject pins 53a, and the other end biases the head portion 53d in the upward direction.

The measuring part 541 is, as a whole, incorporated in the nozzle head 161, and a portion of the measuring part 541 is formed within the nozzles 181 and is movable together with the nozzles 181. A unit for receiving light 541a and a unit for irradiation 541b of the measuring part 541 are mounted on the head base portion 16a, and are optically connected to the nozzles via optical fibers 541c, 541d, 541e, and 541f, linking the nozzles 181 and the nozzle head 161.

FIG. 4 is a drawing showing the nozzle head 161, the X axis transfer mechanism 401x, and the Y axis transfer mechanism 401y according to the first embodiment.

As shown in FIG. 4A, the X axis transfer mechanism 401x has: an X axis motor 46a provided on a Y axis drive plate 45 driven by the Y axis transfer mechanism 401y mentioned below; a pulley 46b that is rotatingly driven by means of the X axis motor 46a; a pulley 46c that is axially supported by the Y axis drive plate 45; a timing belt that is suspended over the interval between the two pulleys 46b and 46c; an X axis drive plate 44 that is joined with the XY axis movable body 41 and is movable along the X axis direction by means of the timing belt 46; and a guide rail 44a that guides the X axis drive plate 44 along the X axis direction of the Y axis drive plate 45. The two holes 47 piercingly provided on the Y axis drive plate 45 respectively penetrate the two shafts 48 mentioned below, and the Y axis drive plate 45 is guided by a shaft 48 and is movable along the Y axis direction.

As shown in FIG. 4B, the Y axis transfer mechanism 401y has: the two shafts 48, in which both ends are supported by shaft fixing blocks 48a and 48b that are supported by the main body of the multi function dispensing unit 111; a Y axis motor 49a that, in the same manner as the fixing block 48b, is supported by the main body of the multi function dispensing unit 111; a pulley 49b that is rotatingly driven by means of the Y axis motor 49a; a pulley 49c that is axially supported by the main body; a timing belt 49 that is suspended over the interval between the two pulleys 49a and 49b; and a Y axis drive plate 45 that is driven in the Y axis direction by means of the timing belt 49.

FIG. 5 shows a nozzle 181 of the automated nucleic acid processor 101 shown in FIG. 2 to FIG. 4.

The nozzle 181 has: a cavity 181a provided in the interior; a lower portion 181c as the end portion provided with a measuring end 521 that receives light based on changes in the optical state, such as light emissions, in which a dispensing tip 261, a tip for separating 262, or a tip for punching 271 is mountable by being detachably fitted; an upper portion 181b having a larger outer diameter than the lower portion 181c; a vent piping 181d in which gases are able to pass through the interior, that is provided such that it laterally protrudes from the side surface of the upper portion 181b and is joined to the cavity 181a; and a plug 181h provided such that it fits the aperture of the lower end of the cavity 181a, and in which gaps 181e, 181f, and 181g at three positions for venting that communicate the cavity 181a with the exterior are formed in the interval with the aperture.

The nozzle 181 further has a heating portion 511 provided such that it surrounds the outer peripheral surface of the upper portion 181b thereof, and a portion of the measuring part 541 including the measuring end 521 is provided in the interior thereof. The measuring part 541 has: three optical fibers for irradiation 541c, 541d, and 541e, in which the ends 521c, 521d, and 521e are exposed to the lower end surface of the plug 181h, that penetrate the nozzle 181 through the cavity 181a of the nozzle 181 along the axial direction of the nozzle 181, and arranged such that they achieve a central angle of approximately 120 degrees with the axis of the nozzle as the center; and an optical fiber for receiving light 541f, in which the end 521f is exposed to the lower end surface of the plug 181h, that penetrates the nozzle 181 through the cavity 181a along the axis of the nozzles 181. The other end of the optical fibers for irradiation 541c to 541e are connected to the unit for light source irradiation 541b, in which three types of light sources are built-in, and the other end of the optical fiber for receiving light 541f is connected to the unit for receiving light 541a for example. It is preferable to provide a selection device within the unit for receiving light 541a comprising a plurality of filters that select a wavelength or a wavelength range of the light input from the optical fiber for receiving light 541f. According to the present embodiment, a plurality of types of fluorescent compounds can be identified.

FIG. 6 is a drawing showing the state at the time of a measurement of the real-time PCR. The aperture of the wide-mouthed piping part 221b of the reaction vessel 221 of the container 201 is blocked by mounting the sealing lid 301 on the lower portion 181c of the nozzle 181. The amplification solution 33 is housed in the narrow piping part 221a of the reaction vessel 221, and becomes sealed within the reaction vessel 221 by means of the sealing lid 301. The temperature controller 601 is provided on the lower side of the reaction vessel 221. The temperature controller 601 has; a heat block 601a having an indentation with a shape fitting the narrow piping part 221a of the reaction vessel 221, a Peltier element 601b that is able to heat and cool the heat block 601a, and a heat sink 601c. In the present embodiment, by incorporating not just the measuring end 521, but the entire measuring part 541 into the nozzle head 161 and joining it to the nozzle 181, the device lifetime is long since the components of the measuring part 541, including the optical fibers 541c, 541d, 541e, and 541f, are not deformed or do not become mutually shifted as a result of the movement of the nozzles 181.

FIG. 7 is a drawing showing a state in which a reaction vessel is blocked at the time of a measurement of the real-time PCR of the nucleic acids or the fragments thereof, and the amplification solution 33 is sealed within the reaction vessel.

FIG. 7A is a drawing showing a state in which the amplification solution 33 housed in the reaction vessel 220 is sealed using just the sealing liquid 29. In this case, since the aperture of the reaction vessel 220 is narrow and the surface tension of the sealing liquid 29 is smaller than that of water or the material of the vessel, a curved liquid surface with a comparatively large curvature is formed. Consequently, in a case where the optical state, such as light emissions, within the amplification solution 33 is measured from the upper side of the sealing liquid 29, there is a concern of the light being scattered due to this curved liquid surface, and a clear and high-accuracy measurement not being able to be performed. Therefore, in this case, it is preferable to perform the measurement of the optical state from the side surface of the reaction vessel 220.

FIG. 7B is a drawing showing a state in which the amplification solution 33 housed within the reaction vessel 221 is sealed using just the sealing liquid 29. In this case, the amplification solution 33 is the amount of liquid that is housed in just the narrow piping part 221a of the reaction vessel 221. On the other hand, an amount of liquid that reaches the wide-mouthed piping part 221b is used for the sealing liquids 29. In this case, since the sealing liquid 29 expands over the wide aperture area of the wide-mouthed piping part 221b, the effect of the surface tension between the reaction vessel wall surface becomes mutually smaller, and a virtually flat liquid surface is obtained. Consequently, a measurement using the nozzle 183 on the upper side separated from the reaction vessel 221 can be performed clearly and with a high-accuracy. The temperature controller 601 is provided on the lower side of the reaction vessel 221.

FIG. 7C shows a case where, for the amplification solution 33 housed within the reaction vessel 221, the sealing liquid 29 and the sealing lid 301 are both used to seal the amplification solution 33 housed in the narrow piping part 221a. In this example, a case is shown in which a bottom surface 301b of the sealing lid 301 does not make contact with the sealing liquid 29, and is separatingly sealed via an air layer.

FIG. 7D shows a state where, for the amplification solution 33 housed within the reaction vessel 221, the sealing liquid and the sealing lid 302 are both used to seal the amplification solution 33 housed in the narrow piping part 221a. In this example, the bottom surface 302a of the sealing lid 302 has a transparency in the same manner as the sealing lid 301. However, in contrast to the sealing lid 301, the central portion thereof is indented in the downward direction. Therefore, it makes contact with the sealing liquid 29 in the sealed state, and an air layer is not formed between the sealing liquid 29 and the central portion of the bottom surface 302a. Consequently, the effects of the interface between the sealing liquid 29 and the air layer on the light from the amplification solution 33, such as scattering, refraction, and reflection as a result of surface tension, can be removed, and a clear light can be transmitted.

FIG. 8 is a plan view showing enlarged, a series of housing parts of the container 201, which represents the first embodiment of the container 20, provided on the stage 17 of the multi function dispensing unit 111.

The container 201 is provided with the longitudinal direction thereof along the Y axis direction, and comprises two cartridge vessels 241 and 211 aligned along the X axis direction. The cartridge vessel 241 represents a liquid housing part group wherein reaction vessels and liquid housing parts are arranged in a single row form. The cartridge vessel 211 represents a housing parts for instruments group wherein various instruments used by mounting on the nozzle 181 of the multi function dispensing unit 111 are arranged in a single row form.

The cartridge vessel 241 has, as the reaction vessel group 22, four reaction vessels 221 for PCR amplification and two reaction vessels 222 maintained at a predetermined temperature by means of a constant temperature controller 611 mentioned below, housing parts for reagents and the like 231 comprising ten liquid housing parts, and a liquid housing part group 232 comprising four tubes. The volume of the reaction vessels 221 is of the order of approximately 200 µL, and the volume of the other reaction vessels, the liquid housing parts, and the tubes is of the order of approximately 2 mL.

The reaction vessels 221 are used for the amplification of nucleic acids or fragments thereof, and temperature control is performed by means of the temperature controller 601 based on a predetermined amplification method. The reaction vessel 221 is formed with two levels as shown in FIG. 6, and has a narrow piping part 221a provided on the lower side in which the amplification solution 33 is housed, and a wide-mouthed piping part 221b provided on the upper side, which is communicated with the narrow piping part 221a and has an aperture that is wider than the aperture of the narrow piping part 221a, in which the sealing liquid 29 is housed. The four reaction vessels 221 are covered with a film 221c that is detachable by the hand of a user, which prevents contamination of the reaction vessels 221. The inner diameter of the wide-mouthed piping part 221b is 8 mm for example, and the inner diameter of the aperture of the narrow piping part 221a is of the order of 5 mm for example.

The housing parts for reagents and the like 231 house seven types of solutions for separating and extracting 32 in the following manner. It has a liquid housing part 231J that houses 1.2 mL of distilled water, a liquid housing part 231G that houses a dissociation liquid, a liquid housing part 231F that houses 700 µL of a washing liquid 2, a liquid housing part 231E that houses 700 µL of a washing liquid 1, a liquid housing part 231C that houses 500 µL of a binding buffer solution, a liquid housing part 231B that houses 200 µL of Lysis 2, a liquid housing part 231A that houses 40 µL of Lysis 1, a liquid housing part 231D that houses a magnetic particle suspension 31, and liquid housing parts 231I and 231H that are initially empty. The apertures of these ten housing parts for reagents and the like 231 in total are prepacked with the respective reagents, and the like, by being covered by a punchable film 231a.

The liquid housing part group 232 detachably retains five tubes 232A, 232B, 232C, 232D, and 232E in five holes piercingly provided in the substrate 241a. The respective holes have: the tube 232E in which 200 µL of a sample 35 of a suspension of bacteria, cells, and the like, or whole blood for example is housed; the tube 232D in which 150 µL of mineral oil is housed as the sealing liquid 29 for sealing the amplification solution 33 housed in the reaction vessels 221; the tube 232C in which 1300 µL of isopropyl alcohol (i-Propanol) used in the removal of protein and the like, is housed as the solution for separating and extracting 32; the tube 232B in which 70 µL of a master mix (SYBR (registered trademark) Green Mix) consisting of enzymes, buffers, primers and the like, is housed as the amplification solution 33; and the empty tube 232A in which extracted nucleic acids or fragments thereof can be housed.

To the cartridge vessel 241, a QR (registered trademark) code representing identification data is attached in the identification data display portion 281. The identification data comprises sample information and testing information. The sample information comprises; the name of the patient from which the sample was extracted, an ID number, an extraction date, and the like. The testing information contains testing items such as the identification of the influenza virus, genetic testing, the type of reagent to be tested for, and the production lot number of the reagent. The cartridge vessel 241 integrally forms the reaction vessel group 221, the housing parts for reagents and the like 231, and the substrate 241a. The respective tubes of the liquid housing part group 232 are detachably retained by five holes piercingly provided in the substrate 241a.

On the other hand, the cartridge vessel 211 has: a housing part 211G that houses sealing lids 301 for sealing the amplification solution 33 housed by blocking the aperture of the reaction vessel 221 and that are mountable on the lower portion 181c of the nozzles 181; four tip housing parts 211C, 211D, 211E, and 211F that house dispensing tips 261 having a volume of the order of 200 µL; a tip housing part 211B that houses tips for separating 262, which is a type of dispensing tip with a volume of the order of 1 mL; and a tip housing part 211A that houses tips for punching 271, which are able to punch the film 231a. The apertures of these housing parts 211A to 211G are covered with a film 211b, and the sealing lids 301, the four dispensing tips 261, the tips for separating 262, and the tips for punching 271 are sealed in these housing parts beforehand. The film 211b is detachable from the substrate 211a by the hand of a user. The substrate 211a of the cartridge vessel 211 and the respective housing parts 211A to 211G are integrally formed.

In the cartridge vessel 211, housing parts are not provided in the section adjacent in the X axis direction to the section in which the reaction vessel group 221 of the cartridge vessel 241 arranged in parallel is provided. This is, as mentioned below, in a case where the measuring end and the nozzle are provided parallel with a spacing in the X axis direction, to avoid tips becoming mounted on the nozzle or the nozzle and the tips making contact at the time measurements are performed with respect to the vessel 221 by means of the measuring end. As another example, it is acceptable for a housing part that houses sealing lids 301 for sealing the respective reaction vessels 221 to be provided in the section adjacent in the X axis direction to the section in which the reaction vessel group 221 is provided. This is because, in this case, the sealing lids 301 are mounted on the reaction vessel 221, and the housing part is empty.

FIG. 9 is a drawing showing an automated nucleic acid processor using a multi function dispensing unit 102 according to a second embodiment.

The automated nucleic acid processor using a multi function dispensing unit 102 has: a nozzle 182 through which a flow path 182a in which gases are able to pass through the interior, penetrates; as the suction-discharge mechanism 50 that performs the suction and the discharge of gases, a cylinder 502b that is connected with the nozzle 182 and the flow path 182a via a piping 502a and in which a piston is slidable in the interior; a piston rod 502c in which a piston 502d is provided on one end; a heating portion 511 for heating the sealing lid 301 mounted on the nozzle 182; and a measuring part 542 whereby the optical state, including light emissions, colors, color changes, or light variations generated within the amplification solution sealed within the reaction vessel 221, is measurable.

Dispensing tips 261, tips for separating 262, and tips for punching 271 are mounted by detachably fitting to the lower portion 182c of the nozzles 182, and the lower ends thereof correspond to a measuring end 522 that receives the light based on changes in the optical state, such as light emissions. The upper side of the nozzle 182 is provided with an upper portion 182b having a larger outer diameter than the lower portion 182c. The heating portion 511 is provided along the outer peripheral surface of the upper portion 182b near the lower portion 182c, and by heating the sealing lid 301 mounted on the lower portion 182c, condensation on the sealing lid 301 is prevented.

Furthermore, the interior of the nozzle 182 is provided with an optical fiber for receiving light 542c and an optical fiber for irradiation 542d extending from the lower portion 182c, which represents the end portion, to a void portion 182e provided along the axis of the nozzle 182 and in the middle of the upper portion 182b, and from the void portion 182e through a joined portion 182d to exit to the exterior of the nozzle 182, reaching the light receiving unit 542a and the irradiation unit 542b. The flow path 182a is provided in a position that does not pass through the void portion 182e. Furthermore, the other ends of the optical fiber for receiving light 542c and the optical fiber for irradiation 542d are connected to a rod lens 542e in the interior of the lower portion 182c of the nozzle 182, becoming the measuring end 522.

FIG. 10 is a drawing showing a state in which a dispensing tip 261 and a tip for separating 262 are mounted on the nozzle 182 of the automated nucleic acid processor using a multi function dispensing unit 102, according to the second embodiment.

A cartridge vessel 202 is provided on the stage of the device 102 as the container 20. The cartridge vessel 202 has a plurality of holes piercingly provided in the substrate 202a, and is such that in the respective holes: an integrally formed liquid housing part group 202b comprising housing parts for reagents and the like 234 and reaction vessels 222; a separately formed reaction vessel 221; and a separately formed sealing lid 301 are made to be fitted and retained.

In the drawing, from the right side, the reaction vessel 221, a sealing lid 301 housed within the reaction vessel 221, a reaction vessel group 222 comprising two reaction vessels, and housing parts for reagents and the like 234 comprising ten liquid housing parts are fittingly retained in the respective holes. The reaction vessels 221 are, as mentioned above, formed from the two levels of the narrow piping part 221a and the wide-mouthed piping part 221b. The heat block 601a of the temperature controller 601 is provided on the lower side of the narrow piping part 221a of the reaction vessel 221, and temperature control of the sealed amplification solution is achieved through the heat block 601a fitted to the outer bottom portion of the narrow piping part 221a. The sealing lid 301 for sealing the amplification solution housed within the reaction vessel 221 is retained such that it fits a hole for sealing lid retention 251 piercingly provided in the substrate 202a. An annular protrusion 301a is formed along the outer peripheral side surface of the sealing lid 301, and the sealing performance at the time the wide-mouthed piping part 221b of the reaction vessel 221 is fitted is increased. At the very least, the bottom surface 301b of the sealing lid 301 has a transparency, and the optical state within the reaction vessel 221 is made measurable via the sealing lid 301. Furthermore, the concave portion on the upper side of the sealing lid 301 is a fitting portion 301c to which the lower portion 182c of the nozzle 182 is fittable.

All of the apertures of the reaction vessel group 222 and the housing parts for reagents and the like 234 of the liquid housing part group 202b are covered with a film for pre-packing 202c, and prevent the evaporation and contamination of the liquids. The lower side of the reaction vessel group 222 is provided with the heat block of the constant temperature controller 611, and temperature control is achieved through the heat block fitted to the outer bottom portion of the respective liquid housing parts of the reaction vessel group 222.

The tip for separating 262 mounted on the nozzle 182, as shown in FIG. 10B, aspirates the magnetic particle suspension 31 while moving along the Y axis direction, which is the longitudinal direction of the cartridge vessel 202, adsorbs the magnetic particles to the inner walls thereof by applying a magnetic field within the narrow diameter piping thereof by means of a magnet 15a, and performs processing while moving to the next liquid housing part.

FIG. 11A is a drawing showing a state in which, by using the nozzle 182, and with respect to the sealing lid 301 housed in the hole for sealing lid retention 251 of the cartridge vessel 202, which represents the container shown in FIG. 10, following positioning of the nozzle 182 on the upper side thereof, the sealing lid 301 is mounted by fitting to the lower portion 182c of the nozzle 182 by lowering the nozzle 182 by means of the Z axis transfer mechanism, and next, by means of the Y axis transfer mechanism, is moved in the Y axis direction of the container 202 and positioned on the reaction vessel 221.

FIG. 11B is a drawing showing the measurement state of real-time PCR, and shows a state in which the amplification solution 33 housed within the narrow piping part 221a of the reaction vessel 221 is sealed by lowering the nozzle 182 mounted with the sealing lid 301, toward the reaction vessel 221 by means of the Z axis transfer mechanism, and fitting the sealing lid 301 to the wide-mouthed piping part 221b of the reaction vessel 221.

The narrow piping part 221a is temperature controlled by fitting to the indentation of the heat block 601a. In this case, the heating portion 511 is heated such that the light based on changes in the optical state within the reaction vessel 221 is made receivable by means of the measuring end 522 of the measuring part 542, and such that condensation does not occur on the bottom surface 301b of the sealing lid 301.

The narrow piping part 221a is temperature controlled by fitting to the indentation of the heat block 601a. In this case, the heating portion 511 is heated such that the light based on changes in the optical state within the reaction vessel 221 is made receivable by means of the measuring end 522 of the measuring part 542, and such that condensation does not occur on the bottom surface 301b of the sealing lid 301. In the present embodiment, since the flow path 182a and the optical fibers 542c and 542d are provided such that they do not make contact, the effect of the fluid toward the optical fibers can be ignored. Furthermore, by providing the rod lens 542e, a wide range of optical states can be measured.

FIG. 12 shows a cartridge vessel 203 according to a third embodiment corresponding to the container 20 mounted on the stage 17 of the automated nucleic acid processor using a multi function dispensing unit 101 shown in FIG. 2. The cartridge vessel 203 differs from the cartridge vessel 202 according to the second embodiment, and is formed by integrally molding the substrate 203a and the respective housing parts.

As shown in the cross-sectional view of FIG. 12A, from the right side, the reaction vessel 221, a sealing lid housing part 252 that stores sealing lids 301 for sealing the housed amplification solution 33 within the reaction vessel 221 by blocking the aperture of the reaction vessel 221, a reaction vessel group 224 comprising two liquid housing parts, and housing parts for reagents and the like 236 comprising ten liquid housing parts, are provided. The apertures of the reaction vessel 221 and the sealing lid housing part 252 which houses the sealing lid 301, are covered by a film for pre-packing 203d that is able to be peeled off by the hand of a user. Furthermore, the apertures of the reaction vessel group 224 and the housing parts for reagents and the like 236 are covered by a film for pre-packing 203b that is punchable by the tip for punching 271. FIG. 12B shows a state before the film 203d is peeled off, and FIG. 12C after it is peeled off. The edge 203c of the film 203d is not pasted to the substrate 203a such that it is easy to peel off.

FIG. 13 shows an automated nucleic acid processor using a multi function dispensing unit 103 according to a fourth embodiment.

FIG. 13A is a drawing showing an external view of the automated nucleic acid processor 103, and is the same as the device 101 according to the first embodiment, although the displayed content and the operation of the control panel 192 are different. Here, elements that are the same as the first embodiment are represented by the same reference symbols, and the descriptions thereof are omitted.

FIG. 13B is a drawing showing a state in which the door 12 is opened, and a multi function dispensing unit 113 is provided in the interior of the enclosure 14. Furthermore, the multi function dispensing unit 113 has: a nozzle head 163 corresponding to the nozzle head 16, which is provided with one or two or more (one in this example) nozzles 183 corresponding to the nozzles 18, a suction-discharge mechanism 503 corresponding to the suction-discharge mechanism 50, and a magnetic force part 151 corresponding to the magnetic force part 15; the container 201 according to the first embodiment provided on the stage 17; a transfer mechanism 401 corresponding to the transfer mechanism 40, which is movable in the X axis, Y axis, and Z axis directions with respect to the container 201; and a measuring part 543 provided on the nozzle head 163 that is able to measure the optical state, including light emissions, colors, color changes, or light variations generated within the reaction vessels provided in the container 201.

FIG. 14 is a drawing showing the nozzle head 163 and, of the transfer mechanism 401, the X axis transfer mechanism 401x that performs movement in the X axis direction, and the Z axis transfer mechanism 401z that performs movement in the Z axis direction. Furthermore, the Y axis transfer mechanism 401y that performs movement in the Y axis direction is the same as in FIG. 4B, and is omitted.

The nozzle head 163 according to the present embodiment has: a head base portion 163 that is movable in the X, Y, and Z axis directions with respect to the container 201; a nozzle 183 provided on a bottom plate 163b joined to the head base portion 163a, to which the respective apertures for mounting 261d of the dispensing tip 261, the tip for separating 262, and the tip for punching 271 (refer to FIG. 10) are mountable; a suction-discharge mechanism 503 that is communicated with the flow path of the nozzle 183, whereby the suction and the discharge of air is possible via the nozzle 183; a detaching mechanism 531 provided on the head base portion 163a that makes possible the detaching of the dispensing tip 261 and the like, mounted on the end portion of the nozzle 183; and a measuring part 543 mounted as a whole on the head base portion 163a such that it is linked with the nozzle 183, in which a measuring end 523 that receives the light based on changes in the optical state is provided on the lower side of the bottom plate 163b separated from the end portion of the nozzle 183 by leaving a predetermined spacing along the X axis direction. Here, the predetermined spacing is the respective widths of the cartridge vessel 241 and the cartridge vessel 211 shown in FIG. 8, or a length that is shorter than the center-to-center distance of the X axis lengths for example, such as half the length thereof.

The suction-discharge mechanism 503 has: a P axis motor 503a; a ball screw 503b in which one end is joined to the P axis motor 503a and is rotatingly driven by means of the P axis motor 503a, and the other end is axially supported by the head base portion 163a; a P axis drive plate 503c that threads with the ball screw 503b and is raised and lowered along the Z axis direction by means of the rotation of the ball screw 503b; a cylinder 503d that is directly communicated with the nozzle 183 and in which a piston is slidably provided in the interior; and a piston rod 503e in which the piston is provided on one end, and the other end is joined to the P axis drive plate 503c. Within the nozzle 183, a flow piping communicated with the cylinder 503d is provided along the axial direction thereof.

As shown in FIG. 15, the measuring part 543 is mounted as a whole on the bottom plate 163b of the nozzle head base portion 163a such that it is linked with the nozzle 183. The measuring part 543 has a dark box 543j and a light guide piping 543a that downwardly protrudes from the dark box 543j in which light is able to pass through the interior, and to which the measuring end 523 is provided on the lower end. The interior of the dark box 543j has: an irradiation unit 543c for irradiating excitation light, provided on the upper end of the light guide piping 543a, a branched piping 543k that branches to the side of the light guide piping 543a, a light receiving unit 543d that is optically connected to the light guide piping 543a via the branched piping 543k, a dichromatic mirror 543b provided within the light guide piping 543a that, of the light incident from the measuring end 523, reflects and guides to the branched piping 543k only the light having a predetermined wavelength, and transmits the light of all other wavelengths, a filter plate 543e provided such that it partitions the branched piping 543k and in which a plurality (four in this example) of filters are arranged, a filter plate drive plate 543f that is joined to the filter plate 543e and is able to be raised and lowered along the Z axis direction, a ball screw 543g that is threaded with the drive plate 543f and raises and lowers the drive plate 543f by means of rotation, and a motor 543h that rotatingly drives the ball screw 543g. Consequently, the strength of fluorescence of a plurality of types of wavelengths or wavelength ranges can be measured.

A reaction vessel 221 comprising a narrow piping part 221a housing an amplification solution and a wide-mouthed piping part 221b housing the sealing liquid 29, which has a transparency, is positioned on the lower side of the measuring end 523, and the amplification solution 33 is sealed within the reaction vessel 221 by means of the sealing liquid 29. In the present embodiment, a selection device comprising a plurality of filters and the like, whereby the wavelength or the wavelength range of the received light can be selected, is provided within the measuring part 543. Therefore a plurality of types of fluorescent compounds can be identified. Furthermore, in the present embodiment, not just the measuring end 523, but the entire measuring part 543 is incorporated into the nozzle head 163, and is linked with the nozzle 181. Therefore, the measuring part 543 does not become deformed as a result of the movement of the nozzle 183, and hence the device lifetime is long.

FIG. 16 shows a measuring part 544 according to a fifth embodiment. The measuring part 544 is, in the same manner as the measuring part 543 of the fourth embodiment, mounted as a whole on the nozzle head 163 such that it is linked with the nozzle 183, and is able to measure the optical state, including light emissions, colors, color changes, or light variations generated within the reaction vessels. A measuring end 524 that receives the light based on light emissions and the like, is provided on the lower side of the bottom plate 163b separated from the end portion of the nozzle 183 by leaving a predetermined spacing along the X axis direction.

The measuring part 544 has a dark box 544j and a light guide piping 544a that downwardly protrudes from the dark box 544j in which light is able to pass through the interior, and to which the measuring end 524 is provided on the lower end. The interior of the dark box 544j has; a light receiving unit 544d provided such that it connects at the upper end of the light guide piping 544a, a dichromatic mirror 544b provided within the light guide piping 544a that, of the light incident from the measuring end 524, reflects and guides to the branched piping 544i only the light having a predetermined wavelength, and transmits the light of all other wavelengths, an irradiation unit 544c for irradiating excitation light connected to the light guide piping 544a via the branched piping 544i, a filter plate 544e provided such that it partitions the connection section between the light receiving unit 544d and the upper end of the light guide piping 544a and in which a plurality (four in this example) of filters are arranged, a filter plate drive plate 544f that is joined to the filter plate 544e and is able to be raised and lowered along the Y axis direction, a ball screw 544g that is threaded with the drive plate 544f and raises and lowers the drive plate 544f by means of rotation, and a motor 544h that rotates the ball screw 544g. The reaction vessel 221 mentioned above is positioned on the lower side of the measuring end 524.

FIG. 17 shows a measuring part 545 according to a sixth embodiment. The measuring part 545 is, in the same manner as the measuring part 543 of the fourth embodiment and the measuring part 544 of the fifth embodiment, mounted as a whole on the nozzle head 163 such that it is linked with the nozzle 183, and is able to measure the optical state, including light emissions, colors, color changes, or light variations generated within the reaction vessels. It has a measuring end 525 that receives the light based on light emissions and the like, on the lower side of the bottom plate 163b, which is joined with the head base portion 163, leaving a predetermined spacing along the X axis direction with the end portion of the nozzle 183.

The measuring part 545 has a dark box not shown in the drawing, such as that shown in FIG. 15 or FIG. 16, and a light guide piping 545a that downwardly protrudes from the dark box in which light is able to pass through the interior, and to which the measuring end 525 is provided on the lower end. The interior of the dark box has; an irradiation unit 545c for irradiating excitation light, provided on the upper end of the light guide piping 545a and optically connected to the light guide piping 545a, a branched piping 545i that branches to the side of the light guide piping 545a, a light receiving unit 543d that is optically connected to the light guide piping 545a via the branched piping 545i, a dichromatic mirror plate 545b having two types of dichromatic mirrors provided within the light guide piping 545a that, of the light incident from the measuring end 525, reflects and guides to the branched piping 545i light having two types of predetermined wavelengths, and transmits the light of all other wavelengths, a translation motor 545j that performs switching driving of the two types of dichromatic mirrors, a filter plate 545e provided such that it partitions the interval between the branched piping 545i and the light receiving unit 545d and in which a plurality (four in this example) of filters are arranged, a filter plate drive plate 545f that is joined to the filter plate 545e and is able to be raised and lowered along the Z axis direction, a ball screw 545g that is threaded with the drive plate 545f and raises and lowers the drive plate 545f by means of rotation, and a motor 545h that rotatingly drives the ball screw 545g. According to the present embodiment, by transmitting irradiation light having two types of wavelengths or wavelength ranges, the fluorescence strength of four types of wavelengths or wavelength ranges can be measured. Therefore, within a single reaction vessel, using a plurality of types of fluorescent compounds under the same conditions, real-time PCR or PCR of a plurality of types of amplification subjects can be performed and measured in parallel.

Next, an automated nucleic acid processor using a multi function dispensing unit 104 according to a seventh embodiment is described based on FIG. 18 and FIG. 19.

FIG. 18A is a drawing showing an external view of the automated nucleic acid processor 104, which has: an enclosure 141 to which a multi function dispensing unit 114 corresponding to the multi function dispensing unit 11 is built into the interior; a door 121 that covers the aperture of the enclosure 141 such that it can be opened and closed; a control panel 193 corresponding to the control panel 19 having a liquid crystal display portion and operation keys provided on the door 121; and an indentation 131 for opening and closing of the door 12.

FIG. 18B is a drawing showing a state in which the door 121 is opened. The interior of the enclosure 141 is provided with the multi function dispensing unit 114. The multi function dispensing unit 114 has: a nozzle head 164 corresponding to the nozzle head 16 provided with four nozzles 183 (183i, 183ii, 183iii, and 183iv), four cylinders (503), and a magnetic force part 152 corresponding to the magnetic force part 15 that is able to simultaneously apply a magnetic force to the narrow diameter piping of the tips for separating 262 mounted on the four nozzles 183; the four containers 201 corresponding to the four nozzles 183, having a reaction vessel group in which the amplification of nucleic acids or the fragments thereof is performed; a transfer mechanism 402 corresponding to the transfer mechanism 40, that makes the four nozzles movable in the X axis, Y axis, and Z axis directions with respect to the respective containers 201; and four measuring parts 543 provided on the nozzle head 164, that are able to measure the optical state, including light emissions, colors, color changes, or light variations generated within the reaction vessels provided in the containers 201.

FIG. 19 shows the positional relationship resulting from the movement of the four nozzles 183 (183i, 183ii, 183iii, and 183iv) and the four measuring parts (543i, 543ii, 543iii, and 543iv) provided on the nozzle head 164, with respect to the containers 201 (201i, 201ii, 201iii, and 201iv) provided on the stage 17.

The respective nozzles 183i, 183ii, 183iii, and 183iv are such that a single nozzle, the nozzle 183i for example, is set with an exclusive region 17i on the stage 17 corresponding to the nozzle 183i, into which it enters and the other nozzles 183ii, 183iii, and 183iv do not enter. Furthermore, in the same manner as mentioned below, exclusive regions 17ii, 17iii, and 17iv corresponding to the other nozzles 183ii, 183iii, and 183iv are also set.

The containers 201$i$, 201$ii$, 201$iii$, and 201$iv$ are each provided within the exclusive regions 17$i$, 17$ii$, 17$iii$, and 17$iv$. The measuring ends 523$i$, 523$ii$, 523$iii$, and 523$iv$ belonging to the respective measuring parts 543 are provided on the nozzle head 164 in the longitudinal direction of the nozzle head 164 from the nozzles 183$i$, 183$ii$, 183$iii$, and 183$iv$, that is to say, leaving a predetermined spacing along the X axis direction, and are linked with the nozzles such that they are included in the exclusive regions in the same manner as the nozzles. Here, the "predetermined spacing" is less than the pitch spacing between the cartridge vessels 241$i$, 241$ii$, 241$iii$, and 241$iv$ of the liquid housing part group belonging to the containers 201$i$, 201$ii$, 201$iii$, and 201$iv$, and the cartridge vessels 211$i$, 211$ii$, 211$iii$, and 211$iv$ corresponding to the adjacent housing parts for instruments group, and corresponds to a larger spacing than the radius of the reaction vessel or the tips mounted on the nozzles.

Here, FIG. 19A represents the maximum X coordinate position in the X axis direction or the leftmost end of the exclusive regions, and FIG. 19B represents the minimum X coordinate position in the X axis direction or the rightmost end of the exclusive regions. These represent the minimum Y coordinate position in the Y axis direction or the uppermost end of the exclusive regions, and FIG. 19C represents the maximum Y coordinate position in the Y axis direction or the lowermost end of the exclusive regions. According to the present embodiment, the movement of the nozzles is confined to within the respective exclusive regions, which prevents cross-contaminations resulting from the differences in the samples with certainty, and processing with a high reliability can be performed.

Next, a series of processing operations related to the nucleic acids of the automated nucleic acid processor using a multi function dispensing unit 101 according to the first embodiment is described. Step S1 to step S16 below correspond to separation and extraction processing.

In step S1, the door 12 of the automated nucleic acid processor using the multi function dispensing unit 101 shown in FIG. 2 is opened, the five holes piercingly provided in the cartridge vessel 241, which represents the series of housing parts 201 representing the container 20 on the stage 17, are made to retain the tubes 232A, 232B, 232C, 232D and 232E, and by means of the user peeling off the film 221$c$ covering the four reaction vessels 221 of the cartridge vessel 241 and the film 211$b$ covering the respective housing parts of the cartridge vessel 211, the cartridge vessel 241 and the cartridge vessel 211 are mounted in parallel. For the detachment of the film 211$b$, with respect to the housing parts that do not house a liquid, the possibility of contaminations of the interior is small if the sections of the film 211$b$ and the film 241$c$ not pasted to the substrates 211$a$ and 241$a$ of the cartridge vessel 211 and the cartridge vessel 241 are provided at the ends (as shown in FIG. 12 for example).

In step S2, following closing of the door 12, the start of the separation and extraction and amplification processing is instructed by means of the operation of the touch panel of the control panel 191 for example.

In step S3, by means of the digital camera 551 representing the identification data reader 55 provided for the nozzle head 161, the identification data comprising a QR code and the like, displayed on the identification data display portion 281 and 361 of the cartridge vessel 241 and the cartridge vessel 211 are read, analyzed by the identification data analysis portion 71 provided in the CPU+program 70 of the automated nucleic acid processor 101, and the correctness of the combinations of the container 201, the processing objective, and the matches and mismatches of the necessary reagents, and the like, are confirmed.

In step S4, when the confirmation of the correctness of the combinations and the like, by means of the analysis of the identification data is completed, the extraction control part 73 provided on the nucleic acid processing controller 72 of the CPU+program 70 of the device 101 instructs the Y axis transfer mechanism 401$y$ to move the nozzle head 161, and to move in the Y axis direction up to the Y coordinate position of the housing part 211A of the cartridge vessel 211 housing the tip for punching 271, and instructs the X axis transfer mechanism 401$x$ such that the nozzle 181 is positioned directly above the housing part 211A. Next, it instructs the Z axis transfer mechanism 401$z$ to lower the lower portion 181$c$ of the nozzle 181 to the aperture for mounting of the tip for punching 271, such that it is fitted and mounted.

In step S5, punching is performed by repeating with respect to the ten liquid housing parts 231A to 231J and the two reaction vessels 222 covered by the film 231$a$, the actions of; moving the nozzle 181 mounted with the tip for punching 271 onto the cartridge vessel 241 by means of the X axis transfer mechanism 401$x$, moving along the Y axis direction using the Y axis transfer mechanism 401$y$ to the liquid housing part 231A of the liquid housing part group 231 covered by the film 231$a$, and punching it by lowering the tip for punching 271 by means of the Z axis transfer mechanism 401$z$ and raising it again.

In step S6, the nozzle 181 is moved again to the tip for punching housing part 211A of the cartridge vessel 211 by means of the X axis transfer mechanism 401$x$, and by lowering the tip removal plate 53$c$ by lowering the P axis drive plate 501$c$ and lowering the inject pin 53$a$ of the detaching mechanism 531, the tip for punching 271 is detached from the lower portion 181$c$ of the nozzle 181, and housed in the tip housing part 211A.

In step S7, the tip for separating 262 is mounted on the lower portion 181$c$ of the nozzle 181 by moving the nozzle 181 in the Y axis direction along the cartridge vessel 211 and, after reaching the housing part 211B, by lowering the nozzle 181 by using the Z axis transfer mechanism 401$z$. Following raising by means of the Z axis transfer mechanism 401$z$, the tip for separating 262 is moved by using the Y axis transfer mechanism 401$y$ and the X axis transfer mechanism 401$x$, and after reaching the liquid housing part 231J, the narrow diameter piping 262 of the tip for separating 262 is loweringly inserted by means of the Z axis transfer mechanism 401$z$. Furthermore, by raising the P axis drive plate 501$c$ of the suction-discharge mechanism 501, 50 μL is aspirated from the distilled water housed in the liquid housing part 231J, and following raising again of the tip for separating 262 to the upper side of the liquid housing part 231J, the tip for separating 262 is moved by means of the Y axis transfer mechanism 401$y$. Once it is positioned over the liquid housing part 231H, it is lowered and the water is discharged into the liquid housing part 231H, which is housed as a dissociation liquid. In the same manner, 350 μL of water from the liquid housing part 231J is housed in the liquid housing part 231F.

In step S7, additionally, to the solution component (NaCl, SDS solution) housed beforehand in the liquid housing part 231C and the liquid housing part 231E, and the distilled water housed in the liquid housing part 231F, as mentioned above, by aspirating a predetermined amount of isopropanol from the tube 232C and respectively dispensing predetermined amounts to the liquid housing part 231C, the liquid housing part 231E, and the liquid housing part 231F, 500 μL of a binding buffer solution (NaCl, SDS, i-Propanol), 700 μL of a washing liquid 1 (NaCl, SDS, i-Propanol), and 700 μL of a washing liquid 2 (water 50%, i-Propanol 50%) representing the solutions for separating and extracting 32 are respectively prepared within the liquid housing parts 231C, 231E, and 231F.

In step S8, after moving the tip for separating 262 to the tube 232E in which the sample 35 is housed, by using the Y axis transfer mechanism 401y, the end of the tip for separating 262 is inserted within the tube 232E by using the Z axis transfer mechanism 401z. Following the suspension of the sample 35 within the liquid by repeating the suction and the discharge of the suspension of the sample 35 by using the suction-discharge mechanism 501, the sample suspension is aspirated within the tip for separating 262. The sample suspension is moved along the Y axis by means of the Y axis transfer mechanism 401y, to the liquid housing part 232A housing the Lysis 1 (enzyme) representing the solution for separating and extracting 32, and the narrow diameter piping of the tip for separating 262 is inserted through the hole in the punched film 231a, and the suction and the discharge is repeated such that the sample suspension and the Lysis 1 are stirred.

In step S9, the entire amount of the stirred liquid is aspirated by the tip for separating 262, and incubation is performed by housing it in the reaction vessel 222A set to 55° C. by means of the constant temperature controller 611. Consequently, the protein contained in the sample 35 is broken down and made a low molecular weight. After a predetermined time has elapsed, the reaction mixture is left in the reaction vessel 222A, the tip for separating 262 is moved to the liquid housing part 231B by means of the Y axis transfer mechanism 401y, and the entire amount of the liquid housed within the liquid housing part 231B is aspirated by using the Z axis transfer mechanism 401z and the suction-discharge mechanism 501, and it is transferred using the tip for separating 262 by means of the Y axis transfer mechanism 401y, and the reaction solution is discharged by penetrating the hole in the film 231a within the reaction vessel 222a with the narrow diameter piping.

In step S10, by stirring the Lysis 2 (guanidine) representing the reaction solution and the other solution for separating and extracting 32 and incubating it within the reaction vessel 222a set to 55° C., the protein is solubilized and the protein is dissolved. Following a predetermined time, the entire amount of the reaction solution is aspirated into the tip for separating 262 and transferred to the liquid housing part 231C by means of the Y axis transfer mechanism 401y, and is discharged through the narrow radius piping inserted by penetrating the hole in the film 231a.

In step S11, by stirring the binding buffer solution (NaCl, SDS, i-Propanol) representing the solution for separating and extracting 32 and the reaction solution housed within the liquid housing part 231C, the solubilized protein is further dehydrated, and the nucleic acids or the fragments thereof are dispersed within the solution.

In step S12, using the tip for separating 262, the narrow diameter piping thereof is inserted into the liquid housing part 231C by penetrating the hole in the film 231a, the entire amount is aspirated and the tip for separating 262 is raised by means of the Z axis transfer mechanism 401z, and the reaction solution is transferred to the liquid housing part 231D, and the magnetic particle suspension 31 housed within the liquid housing part 231D is stirred with the reaction solution. A cation structure in which Na+ ions bind to the hydroxyl groups formed on the surface of the magnetic particles contained within the magnetic particle solution 31 is formed. Consequently, the negatively charged DNA is captured by the magnetic particles.

In step S13, the magnetic particles are adsorbed on the inner wall of the narrow diameter piping 262b of the tip for separating 262 by approaching the magnet 15a of the magnetic force part 151 to the narrow diameter piping 262b of the tip for separating 262. In a state where the magnetic particles are adsorbed to the inner wall of the narrow diameter piping 262b of the tip for separating 262, the tip for separating 262 is raised by means of the Z axis transfer mechanism 401z and is moved from the liquid housing part 231D to the liquid housing part 231E using the Y axis transfer mechanism 401y, and the narrow diameter piping 262b is inserted by penetrating the hole in the film 231a.

In a state where the magnetic force within the narrow diameter piping 262b is removed by separating the magnet 15a of the magnetic force part 151 from the narrow diameter piping 262b of the tip for separating 262, as a result of repeating the suction and the discharge of the washing liquid 1 (NaCl, SDS, i-Propanol) housed in the liquid housing part 231E, the magnetic particles are released from the inner wall, and the protein is washed by stirring within the washing liquid 1. Thereafter, in a state where the magnetic particles are adsorbed on the inner wall of the narrow diameter piping 262b as a result of approaching the magnet 15a of the magnetic force part 151 to the narrow diameter piping 262b of the tip for separating 262 again, the tip for separating 262 is, by means of the Z axis transfer mechanism 401z, moved from the liquid housing part 231E to the liquid housing part 231F by means of the Y axis transfer mechanism 401y.

In step S14, the narrow diameter piping 262b of the tip for separating 262 is inserted by penetrating the hole in the film 231a using the Z axis transfer mechanism 401z. By repeating the suction and the discharge of the washing liquid 2 (i-Propanol) housed in the liquid housing part 231F in a state where the magnetic force within the narrow diameter piping 262b is removed by separating the magnet 15a of the magnetic force part 151 from the narrow diameter piping 262b of the tip for separating 262, the magnetic particles are stirred within the liquid, the NaCl and the SDS is removed, and the protein is washed. Thereafter, in a state where the magnetic particles are adsorbed on the inner wall of the narrow diameter piping 262b by approaching the magnet 15a of the magnetic force part 151 to the narrow diameter piping 262b of the tip for separating 262 again, the tip for separating 262 is, by means of the Z axis transfer mechanism 401z, moved from the liquid housing part 231F to the liquid housing part 231J, in which the distilled water is housed, by means of the Y transfer mechanism 401y.

In step S15, by means of the Z axis transfer mechanism 401z, the narrow diameter piping 262b of the tips for separating 262 is lowered through the hole, and by repeating the suction and the discharge of the water at a slow flow rate in a state in which the magnetic force is applied within the narrow diameter piping 262b of the tip for separating 262, the i-Propanol is substituted by water and is removed.

In step S16, by means of the Y axis transfer mechanism 401y, the tip for separating 262 is moved along the Y axis direction and the narrow diameter piping 262b is inserted into the liquid housing part 231H through the hole in the film 231a. By stirring the magnetic particles by repeating the suction and the discharge within the distilled water, which represents the dissociation liquid in a state where the magnet 15a of the magnetic force part 151 is separated from the narrow diameter piping 262b of the tip for separating 262 and the magnetic force is removed, the nucleic acids or the fragments thereof retained by the magnetic particles are dissociated (eluted) from the magnetic particles into the liquid. Thereafter, a magnetic field is applied within the narrow diameter piping, and the magnetic particles are adsorbed on the inner wall by approaching the magnet 15*a* to the narrow diameter piping 262*a* of the tips for separating 262, and the nucleic acids, and the solution containing the extracted nucleic acids, and the like, is made to remain in the liquid housing part 231H. The tip for separating 262 is moved on the cartridge vessel 211 by means of the X axis transfer mechanism 401*x* and is moved to the housing part 211B by means of the Y axis transfer mechanism 401*y*, and the tip for separating 262, to which magnetic particles are adsorbed, is detached from the nozzle 181 within the housing part 211B together with the magnetic particles as a result of the detaching mechanism 531.

The following step S17 to step S22 corresponds to amplification processing.

In step S17, the nozzle 181 is moved along the Y axis using the Y axis transfer mechanism 401*y* and positioned above the housing part 211C. The nozzle 181 is lowered using the Z axis transfer mechanism 401*z*, and the mounting aperture of the dispensing tip 261 is fitted to the lower portion 181*c* of the nozzle 181, and mounted on the nozzle 181. After moving the dispensing tip 261 in the X axis direction and positioning it on the cartridge vessel 241 by means of the X axis transfer mechanism 401*x*, it is moved along the Y axis direction by means of the Y axis transfer mechanism 401*y* and positioned at the liquid housing part 231H. Using the suction-discharge mechanism 501, 40 µL of a solution containing the nucleic acids or the fragments thereof is aspirated from the liquid housing part 231H and transferred by means of the Y axis transfer mechanism 401*y*, and 10 µL is respectively sequentially dispensed into the four reaction vessels 221. Thereafter, the dispensing tip 261 is moved to above the cartridge vessel 211 by means of the X axis transfer mechanism 401*x*, and the dispensing tip 261 is moved along the Y axis direction by means of the Y axis transfer mechanism 401*y*, and positioned on the housing part 211C, and the dispensing tip 261 is detached into the housing part 211C by means of the detaching mechanism 531.

In step S18, the nozzle 181 is moved along the Y axis direction and positioned on the housing part 211D by means of the Y axis transfer mechanism 401*y*, and by lowering the Z axis transfer mechanism 401*z* and fitting the lower portion 181*c* of the nozzles 181 to the aperture for mounting of a new dispensing tip 261 housed in the housing part 211D, the dispensing tip 261 is mounted on the nozzle 181. After moving the dispensing tip 261 to above the cartridge vessel 241 by means of the X axis transfer mechanism 401*x*, it is moved to the tube 232B by means of the Y axis transfer mechanism 401*y*, 40 µL of the master mix (SYBR Green Mix for example) housed in the tube 232B is aspirated, it is moved along the Y axis direction using the Y axis transfer mechanism 401*y*, and 10 µL is respectively dispensed into the reaction vessels 221. Thereafter, the dispensing tip 261 is moved to the cartridge vessel 211 by means of the X axis transfer mechanism 401*x*, and following further positioning on the housing part 211D by means of the Y axis transfer mechanism 401*y*, the dispensing tip 261 is detached into the housing part 211D by means of the detaching mechanism 531. The solution of the extracted nucleic acids, and the like, and the master mix is housed within the narrow piping part 221*a* of the reaction vessels 221.

In step S19, in the same sequence as the sequence shown in step S18, a new dispensing tip 261 housed in the housing part 211E is mounted on the nozzle 181. After moving the dispensing tip 261 on the cartridge vessel 241 by means of the X axis transfer mechanism 401*x*, it is moved to the tube 232D by means of the Y axis transfer mechanism 401*y*, 80 µL of mineral oil which represents the sealing liquid housed in the tube 232D is aspirated, and it is then moved along the Y axis direction using the Y axis transfer mechanism 401*y*, and 20 µL is respectively dispensed into the reaction vessels 221A, 221B, 221C, and 221D and housed such that it reaches the wide-mouthed piping part 221*b* of the reaction vessels 221A, 221B, 221C, and 221D. Thereafter, the dispensing tips 261 are, in the same manner as mentioned above, detached into the housing part 211E, and are disposed.

In step S20, the nozzle 181 is moved to the housing part 211G by means of the Y axis transfer mechanism 401*y*, lowered by means of the Z axis transfer mechanism 401*z*, and by fitting the lower portion 181*c* of the nozzle to the fitting portion 301*c* of the sealing lid 301 housed in the housing part 211G, it is mounted. The nozzle 181 is moved to the cartridge vessel 241 by means of the X axis transfer mechanism 401*x*, and is fitted and mounted only to the reaction vessel 221D. Thereafter, the reaction vessels 221A, 221B, 221C, and 221D are firstly heated for 10 minutes at 96° C. by means of the temperature controller 601. At that time, the nozzle 181 is detached from the sealing lids 301 by using the detaching mechanism 531, and then sequentially from above the reaction vessels 221A, 221B, 221C, and 221D, changes in the optical state based on light emissions generated within the reaction vessels 221A, 221B, 221C, and 221D are measured via the measuring end 521 provided on the end portion of the lower portion 181*c* of the nozzle 181.

In step S21, a cycle in which the reaction vessels 221 are heated for five seconds at 96° C. and heated for 15 seconds at 60° C. is repeated forty nine times. At that time, in the same manner as step S20, the optical state within the reaction vessels 221 is measured via the measuring end 521.

In step S22, the reaction vessels are heated for two minutes at 74° C. At that time, in the same manner as step S20 and step S21, the optical state is measured. At that time, with respect to the reaction vessel 221D, by pressing the sealing lid 301 using the nozzles 181, the measurement can be performed while blocking with certainty. Furthermore, by shaking the sealing lid 301, condensation can be prevented. Moreover, in a case where measurement is performed via the sealing lid 301, the condensation that occurs on the sealing lid 301 can be prevented by heating the heating portion 511 provided on the nozzle 181.

The foregoing embodiments have been specifically described in order to better understand the present invention, and they are in no way limiting of other embodiments. Therefore, modifications are possible within a scope that does not depart from the gist of the invention. The configurations, shapes, materials, arrangements, amounts, quantities of the nozzles, the dispensing tips, the tips for separating, the tips for punching, the container, the housing parts, the instruments, the measuring end, the measuring part, the suction-discharge mechanism, the transfer mechanism, the magnetic force part, the heating portion, the reaction vessel, the sealing lids, the sealing liquids, and the like, and the utilized reagents and samples are also in no way limited by the examples illustrated in the embodiments. Furthermore, although the nozzles were made to move with respect to the stage, it is possible to also move the stage with respect to the nozzles.

Moreover, the components described in the respective embodiments of the present invention, and the components that form these components, can be appropriately selected, and can be mutually combined by applying the appropriate modifications.

INDUSTRIAL APPLICABILITY

The present invention is related to fields in which the processing, testing, and analysis of nucleic acids, which primarily includes DNA, RNA, mRNA, rRNA, and tRNA for example, is required, and is related to industrial fields, agricultural fields such as food, agricultural products, and fishery processing, chemical fields, pharmaceutical fields, health care fields such as hygiene, insurance, diseases, and genetics, and scientific fields such as biochemistry or biology for example. The present invention is, in particular, able to be used in processing and analysis that handles various nucleic acids, and the like, such as PCR and real-time PCR.

BRIEF DESCRIPTION OF THE REFERENCE SYMBOLS 10, 101, 102, 103, 104 Automated nucleic acid processor using multi function dispensing unit
11, 111, 113, 114 Multi function dispensing unit
15, 151 Magnetic force part
16, 161 Nozzle head
18, 181, 182, 183 Nozzles
19, 191 Control panel
20, (201), 202, 203 Container group (series of housing parts)
21 (211) Housing parts for instruments (group) (cartridge vessels)
22, 221 Reaction vessels (group)
221a Narrow piping part
221b Wide-mouthed piping part
23 Housing parts for reagents and the like
24 (241) Liquid housing parts (group) (cartridge vessels)
26, 261 Dispensing tips (group)
262 Tips for separating
29 Sealing liquids
30, 301 Sealing lids
32 Solution for separating and extracting
33 Amplification solution
40, 401 Transfer mechanism
50, 501 Suction-discharge mechanism
52, 521, 522 Measuring end
53, 531 Detaching mechanism
54, 541 Measuring part
55 (551) Identification data reader (digital camera)
60, 601 Temperature controller
70 CPU+program
72 Nucleic acid processing controller

The invention claimed is:

1. An automated nucleic acid processing method utilizing a multi-function dispensing unit, said method comprising:
transporting amplification solutions from one or two or more liquid housing parts provided in a container group that house the amplification solutions used in nucleic acid amplification to temperature controlled reaction vessels for nucleic acid amplification provided in said container group using;
dispensing tips detachably mounted on nozzles, whereby suction and discharge of liquids with respect to the dispensing tips is possible by means of a suction-discharge mechanism that performs suction and discharge of gases through the nozzles, and
a transfer mechanism that makes an interval between and said nozzles and said container group relatively movable,
and by means of said suction-discharge mechanism and said transfer mechanism, or said transfer mechanism, transporting sealing liquid and/or sealing lids from predetermined housing parts other than said reaction vessels of said container group into said reaction vessels using said nozzles,
sealing said amplification solutions within said reaction vessels, and
performing temperature control of the interior of said reaction vessels.

2. An automated nucleic acid processing method utilizing a multi-function dispensing unit according to claim 1, wherein said container group is further provided with:
two or more liquid housing parts that house a sample, a magnetic particle solution in which magnetic particles that are able to capture nucleic acids or fragments thereof, which represent an amplification subject, are suspended, and a solution for separating and extracting used for the separation and the extraction of said amplification subject; and
one or two or more tip housing parts that house dispensing tips,
and said method comprises:
using said dispensing tips and mixing and reacting said sample and a dissolving solution representing said solution for separating and extracting that breaks down or dissolves protein contained in the sample;
capturing said amplification subject on the magnetic particles by mixing and reacting the reaction mixture and said magnetic particle solution;
separating the magnetic particles by using a magnetic force part provided on a nozzle head and applying a magnetic field within said dispensing tips or the liquid housing parts to thereby adsorb said magnetic particles on an inner wall of the dispensing tips or the liquid housing parts;
making contact between a dissociation solution representing an other separation and extraction solution housed in said container;
dissociating said amplification subject from the magnetic particles; and
housing a solution of the amplification subject in the liquid housing part as a portion of said amplification solution.

3. An automated nucleic acid processing method utilizing a multi-function dispensing unit according to claim 1, comprising, following sealing or at the time of sealing of said amplification solutions in said reaction vessels, making the measuring end to approach said reaction vessels by using said transfer mechanism, and receiving the light within the amplification solutions, and measuring an optical state including light emissions, colors, color changes, or light variations generated within said amplification solutions sealed within the reaction vessels with said sealing liquid and/or the sealing lid.

4. An automated nucleic acid processing method utilizing a multi-function dispensing unit according to claim 3, wherein said measurement step comprises positioning said measuring end provided on said nozzle head on an upper side of said sealing liquid and/or the sealing lid that is sealing said amplification solution within said reaction vessel by using said transfer mechanism, and performing the measurement of the interior of said amplification solution through the sealing liquid and/or the sealing lid, which have a transparency.

5. An automated nucleic acid processing method utilizing a multi-function dispensing unit according to claim 3, wherein said measurement step comprises moving the measuring end which is provided on said nozzle head such that it is separated from the end portion of said nozzles by leaving a predetermined spacing and is linked with the nozzles, and making incident or irradiating via said sealing liquid and/or the sealing lid, light ray bundles corresponding to the width and shape of an aperture of a section of said reaction vessels housing said amplification solutions.

6. An automated nucleic acid processing method utilizing a multi-function dispensing unit according to claim 2, wherein said sealing step comprises, following mounting of said dispensing tips on said nozzles, sealing said amplification solutions within said reaction vessels by using the dispensing tips, said suction-discharge mechanism, and said transfer mechanism to transport a predetermined amount of said sealing liquid from said predetermined housing part of said container group, and discharge it within said reaction vessels.

7. An automated nucleic acid processing method utilizing a multi-function dispensing unit according to claim 2, wherein said sealing, following mounting of dispensing tips on nozzles and housing of said amplification solutions in reaction vessels, is performed by detaching the dispensing tips from the nozzles, mounting said sealing lids on said nozzles using a fitting portion of the sealing lids and transporting them to said reaction vessels, and blocking an aperture of said reaction vessels.

8. An automated nucleic acid processing method utilizing a multi-function dispensing unit according to claim 7, wherein said sealing, when the housing of said amplification solutions within said reaction vessels is completed, has a step for transporting a predetermined amount of said sealing liquid to said reaction vessels, and then detaching the dispensing tips from said nozzles, mounting said sealing lids on said nozzles, transporting to the reaction vessels, and fitting to the apertures thereof.

9. An automated nucleic acid processing method utilizing a multi-function dispensing unit according to claim 3, comprising a step for mounting said sealing lids on said nozzles, transporting to said reaction vessels, and blocking the apertures thereof, and in a state where said sealing lids are mounted on the nozzles, pressing or shaking by means of the nozzles or said suction-discharge mechanism.

10. An automated nucleic acid processing method utilizing a multi-function dispensing unit according to claim 1 comprising, in a case where said sealing liquid is not housed within said reaction vessels, following blocking of the apertures of said reaction vessels with said sealing lids, heating said sealing lids by heating the end portion of said nozzles at the time of temperature control of the reaction vessels.

11. An automated nucleic acid processing method utilizing a multi-function dispensing unit, said method comprising:

from a liquid housing part group housing a sample, a magnetic particle suspension, and a solution for separating and extracting used for the separation and the extraction of nucleic acids and fragments thereof, provided in a container group which with respect to two or more nozzles provided on a nozzle head, is provided within respective exclusive regions in which a single nozzle enters and the other nozzles do not enter, using dispensing tips detachably mounted on said nozzles, a suction-discharge mechanism that performs suction and discharge of gases, and a transfer mechanism that, in addition to making an interval between said nozzles and said container group relatively movable, restricts the movement of the respective nozzles to within said exclusive regions;

transporting said samples and a dissolving solution that breaks down or dissolves protein which represents said solutions for separating and extracting to the reaction vessels and mixing and reacting them;

mixing and reacting said magnetic particle suspension;

capturing on the magnetic particles the nucleic acids or the fragments thereof which represents an amplification subject obtained from the sample;

separating the magnetic particles by applying a magnetic field within said dispensing tips or the liquid housing parts by means of a magnetic force part provided on said nozzle head and adsorbing them on an inner wall thereof;

dissociating the nucleic acids and the fragments thereof by contacting the separated magnetic particles and a dissociation liquid;

housing and mixing the dissociated nucleic acids or the fragments thereof as a portion of amplification solutions in a temperature controllable reaction vessel by means of said suction-discharge mechanism and said transfer mechanism;

sealing said amplification solutions in said reaction vessels with sealing liquid and/or sealing lids housed in said container group by means of said suction-discharge mechanism and said transfer mechanism, or said transfer mechanism;

performing temperature control of said sealed amplification solutions by using said temperature controllable reaction vessel; and measuring an optical state, including light emissions, colors, color changes, or light variations generated within said amplification solutions sealed within said reaction vessel by means of said sealing liquid and/or the sealing lids, by making a measuring end of a measuring part approach said sealed reaction vessels.

* * * * *

UNITED STATES PATENT AND TRADEMARK OFFICE
CERTIFICATE OF CORRECTION

PATENT NO. : 9,797,008 B2
APPLICATION NO. : 14/707900
DATED : October 24, 2017
INVENTOR(S) : Hideji Tajima Page 1 of 1

It is certified that error appears in the above-identified patent and that said Letters Patent is hereby corrected as shown below:

In the Claims

In Claim 1, Column 44, Line 2, after "between" - delete "and".

Signed and Sealed this
Twenty-eighth Day of May, 2019

Andrei Iancu
*Director of the United States Patent and Trademark Office*